United States Patent
Lee et al.

(10) Patent No.: US 10,849,597 B2
(45) Date of Patent: *Dec. 1, 2020

(54) METHOD OF PROVIDING COPY IMAGE AND ULTRASOUND APPARATUS THEREFOR

(71) Applicant: SAMSUNG ELECTRONICS CO., LTD., Suwon-si (KR)

(72) Inventors: Jae-ho Lee, Seoul (KR); Soon-jae Hong, Seongnam-si (KR); Gi-hun Yun, Goyang-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 931 days.

This patent is subject to a terminal disclaimer.

(21) Appl. No.: 14/631,183

(22) Filed: Feb. 25, 2015

(65) Prior Publication Data

US 2015/0164474 A1 Jun. 18, 2015

Related U.S. Application Data

(63) Continuation of application No. 14/205,762, filed on Mar. 12, 2014, now abandoned.

(Continued)

(30) Foreign Application Priority Data

Apr. 11, 2013 (KR) .................. 10-2013-0040025
Jun. 13, 2013 (KR) .................. 10-2013-0067943

(51) Int. Cl.
*A61B 8/00* (2006.01)
*G06F 3/0488* (2013.01)
(Continued)

(52) U.S. Cl.
CPC .............. *A61B 8/463* (2013.01); *A61B 8/462* (2013.01); *A61B 8/465* (2013.01); *A61B 8/467* (2013.01);
(Continued)

(58) Field of Classification Search
CPC ..... A61B 8/0858; A61B 8/4427; A61B 8/462; A61B 8/463; A61B 8/465; A61B 8/467;
(Continued)

(56) References Cited

U.S. PATENT DOCUMENTS 6,259,436 B1 7/2001 Moon
7,489,306 B2 2/2009 Kolmykov-Zotov et al.
(Continued)

FOREIGN PATENT DOCUMENTS

CN 1126021 C 10/2003
CN 101627361 A 1/2010
(Continued)

OTHER PUBLICATIONS

"Complete SMART Board Tutorial", published online Jan. 28, 2010 at https://www.youtube.com/watch?v=dwla8E6jz4g.*
(Continued)

*Primary Examiner* — Christopher L Cook
(74) *Attorney, Agent, or Firm* — Sughrue Mion, PLLC

(57) ABSTRACT

An ultrasound measurement method includes: providing a first object and a second object within an ultrasound image displayed on a touch screen; activating the first object and the second object, to be movable to perform a measurement on the ultrasound image; receiving a touch-and-drag input with respect to at least one of the first and second objects; and displacing a corresponding one of the first and second objects on the ultrasound image in correspondence with the received touch-and-drag input.

16 Claims, 27 Drawing Sheets

Related U.S. Application Data

(60) Provisional application No. 61/779,520, filed on Mar. 13, 2013.

(51) Int. Cl.
  *G06T 7/62* (2017.01)
  *G06F 3/041* (2006.01)
  *G01S 7/52* (2006.01)
  *A61B 8/08* (2006.01)

(52) U.S. Cl.
  CPC .............. *A61B 8/468* (2013.01); *A61B 8/469* (2013.01); *A61B 8/54* (2013.01); *G06F 3/041* (2013.01); *G06F 3/0488* (2013.01); *G06T 7/62* (2017.01); *A61B 8/0858* (2013.01); *A61B 8/4427* (2013.01); *A61B 8/5223* (2013.01); *G01S 7/52073* (2013.01); *G01S 7/52074* (2013.01); *G01S 7/52084* (2013.01); *G06T 2207/10132* (2013.01); *G06T 2207/20104* (2013.01); *G06T 2207/30004* (2013.01)

(58) Field of Classification Search
  CPC ....... A61B 8/468; A61B 8/469; A61B 8/5223; A61B 8/54; G01S 7/52073; G01S 7/52074; G01S 7/52084; G06F 3/041; G06F 3/0488; G06T 2207/10132; G06T 2207/02
  See application file for complete search history.

(56) References Cited

U.S. PATENT DOCUMENTS

| | | | |
|---|---|---|---|
| 7,948,493 B2 | 4/2011 | Klefenz et al. | |
| 8,127,248 B2* | 2/2012 | Ording | G06F 3/0481 715/766 |
| 8,407,606 B1* | 3/2013 | Davidson | G06F 3/0488 345/173 |
| 8,519,963 B2 | 8/2013 | Kocienda et al. | |
| 8,552,999 B2 | 10/2013 | Dale et al. | |
| 8,896,621 B1* | 11/2014 | Sipher | G06F 3/04883 345/418 |
| 9,311,712 B2 | 4/2016 | Fukata | |
| 2002/0018051 A1 | 2/2002 | Singh | |
| 2004/0119763 A1 | 6/2004 | Mizobuchi et al. | |
| 2006/0161846 A1 | 7/2006 | Van Leeuwen | |
| 2007/0299342 A1 | 12/2007 | Hayasaka | |
| 2008/0118237 A1 | 5/2008 | Wegenkittl et al. | |
| 2008/0119731 A1 | 5/2008 | Becerra et al. | |
| 2008/0122796 A1 | 5/2008 | Jobs et al. | |
| 2008/0165160 A1 | 7/2008 | Kocienda et al. | |
| 2008/0221446 A1 | 9/2008 | Washburn | |
| 2009/0043195 A1 | 2/2009 | Poland | |
| 2009/0270868 A1* | 10/2009 | Park | A61B 17/15 606/87 |
| 2010/0004539 A1 | 1/2010 | Chen et al. | |
| 2010/0094132 A1 | 4/2010 | Hansen et al. | |
| 2010/0179427 A1 | 7/2010 | Yamamoto | |
| 2010/0217128 A1 | 8/2010 | Betts | |
| 2010/0235793 A1 | 9/2010 | Ording et al. | |
| 2010/0298701 A1 | 11/2010 | Shin | |
| 2010/0305444 A1 | 12/2010 | Fujii et al. | |
| 2010/0315437 A1 | 12/2010 | Sinclar et al. | |
| 2010/0321324 A1 | 12/2010 | Fukai et al. | |
| 2011/0043434 A1 | 2/2011 | Roncalez et al. | |
| 2011/0066031 A1 | 3/2011 | Lee et al. | |
| 2011/0078597 A1* | 3/2011 | Rapp | G06F 3/04845 715/765 |
| 2011/0107258 A1 | 5/2011 | Chen | |
| 2011/0112399 A1 | 5/2011 | Willems et al. | |
| 2011/0224546 A1* | 9/2011 | Lee | A61B 8/0866 600/443 |
| 2011/0246876 A1 | 10/2011 | Chutani et al. | |
| 2011/0262018 A1 | 10/2011 | Kumar et al. | |
| 2011/0281619 A1 | 11/2011 | Cho et al. | |
| 2011/0295120 A1* | 12/2011 | Lee | A61B 8/0866 600/443 |
| 2012/0030569 A1 | 2/2012 | Migos et al. | |
| 2012/0179039 A1 | 7/2012 | Pelissier et al. | |
| 2013/0012314 A1 | 1/2013 | Ishikawa | |
| 2013/0019201 A1 | 1/2013 | Cabrera-Cordon et al. | |
| 2013/0152013 A1 | 6/2013 | Forstall et al. | |
| 2013/0179816 A1 | 7/2013 | Seo et al. | |
| 2013/0245428 A1 | 9/2013 | Banjanin | |
| 2013/0316817 A1 | 11/2013 | Tanzawa et al. | |
| 2013/0318475 A1 | 11/2013 | Xie | |
| 2013/0324850 A1 | 12/2013 | Petruzzelli et al. | |
| 2013/0331182 A1 | 12/2013 | Tanzawa et al. | |
| 2013/0345563 A1 | 12/2013 | Stuebe et al. | |
| 2014/0098049 A1* | 4/2014 | Koch | G06F 3/016 345/173 |
| 2014/0114190 A1 | 4/2014 | Chiang et al. | |
| 2014/0121524 A1 | 5/2014 | Chiang et al. | |
| 2014/0181753 A1 | 6/2014 | Kamii et al. | |
| 2014/0198055 A1 | 7/2014 | Barkway | |
| 2014/0317545 A1 | 10/2014 | Miyazaki | |
| 2015/0094578 A1 | 4/2015 | Ninomiya et al. | |
| 2015/0141823 A1 | 5/2015 | Lee et al. | |

FOREIGN PATENT DOCUMENTS

| | | |
|---|---|---|
| CN | 102006828 A | 4/2011 |
| CN | 102316263 A | 1/2012 |
| CN | 202235453 U | 5/2012 |
| CN | 102626326 A | 8/2012 |
| CN | 102793565 A | 11/2012 |
| EP | 2191776 A1 | 6/2010 |
| EP | 2 255 730 A1 | 12/2010 |
| EP | 2 532 307 A1 | 12/2012 |
| JP | 10314167 A | 12/1998 |
| JP | 2005-137747 A | 6/2005 |
| JP | 2007-97816 A | 4/2007 |
| JP | 2008-486 A | 1/2008 |
| JP | 2009-510571 A | 3/2009 |
| JP | 2009-207589 A | 9/2009 |
| JP | 2009-213507 A | 9/2009 |
| JP | 2009-213796 A | 9/2009 |
| JP | 2010-142563 A | 7/2010 |
| JP | 2010-269139 A | 12/2010 |
| JP | 2012-19824 A | 2/2012 |
| JP | 2012-203644 A | 10/2012 |
| KR | 10-2006-0072082 A | 6/2006 |
| KR | 10-2010-0110893 A | 10/2010 |
| KR | 10-2011-0029630 A | 3/2011 |
| KR | 10-1095851 B1 | 12/2011 |
| KR | 10-2012-0036420 A | 4/2012 |
| KR | 10-1167248 B1 | 7/2012 |
| KR | 10-1176657 B1 | 8/2012 |
| KR | 10-2013-0018870 A | 2/2013 |
| WO | 2006/040697 A1 | 4/2006 |
| WO | 2009/049363 A1 | 4/2009 |
| WO | 2009/109585 A1 | 9/2009 |
| WO | 2013/148730 A2 | 10/2013 |

OTHER PUBLICATIONS

Communication dated Mar. 26, 2015 issued by the European Patent Office in counterpart European Patent Application No. 14196386.8.
"A Gmail Miscellany", posted online Nov. 14, 2012, accessed online Jul. 21, 2015, 24 pages total.
Communication dated Jul. 31, 2015, issued by the United States Patent and Trademark Office in counterpart U.S. Appl. No. 14/582,415.
Communication dated Aug. 3, 2015, issued by the State Intellectual Property Office of the People's Republic of China in counterpart Chinese Application No. 201410094048.3.
Communication dated Sep. 25, 2015, issued by the European Patent Office in counterpart European Application No. 15172774.0.
Communication dated Oct. 29, 2015 issued by the Korean Intellectual Property Office in counterpart Application No. 10-2013-0040025.

(56) References Cited

OTHER PUBLICATIONS

Communication dated Dec. 19, 2015 issued by the Korean Intellectual Property Office in counterpart Application No. 10-2013-0067943.
"How do I use multi-touch to move more than one object?", available online Feb. 11, 2012, accessed online Dec. 2, 2015, pp. 1-3.
Communication dated Jan. 29, 2016, issued by the United States Patent and Trademark Office in counterpart U.S. Appl. No. 14/582,415.
Communication dated Dec. 16, 2015, issued by the United States Patent and Trademark Office in counterpart U.S. Appl. No. 14/205,762.
Communication dated May 9, 2014, issued by the United States Patent and Trademark Office in counterpart U.S. Appl. No. 14/205,762.
Communication dated Feb. 15, 2016, issued by the Japanese Patent Office in counterpart Japanese Patent Application No. 2015-562903.
Communication dated Mar. 21, 2016, issued by the European Patent Office in counterpart European Patent Application No. 15191427.2.
Communication dated Apr. 28, 2016, issued by the Korean Intellectual Property Office in counterpart Korean Patent Application No. 10-2013-0040025.
Final Office Action mailed from United States Patent and Trademark Office dated Jun. 27, 2016, in U.S. Appl. No. 14/205,762, pp. 1-14.
Communication dated Jun. 13, 2016 issued by the State Intellectual Property Office of P.R. China in counterpart Chinese Application No. 201510552566.X.
Communication dated May 24, 2016 issued by Korean Intellectual Property Office in counterpart Korean Patent Application No. 10-2013-0067943.
Communication dated Oct. 27, 2016, issued by the Korean Intellectual Property Office in counterpart Korean Application No. 10-2013-0040025.
Communication dated Oct. 20, 2016, issued by the European Patent Office in counterpart European Application No. 15191427.2.
Communication dated Oct. 24, 2016, issued by the European Patent Office in counterpart European Application No. 14159249.3.
Communication dated Nov. 24, 2016, issued by the State Intellectual Property Office of P.R. China in counterpart Chinese Application No. 201510552566.X.
Communication dated Mar. 10, 2017 by the State Intellectual Property Office of P.R. China in counterpart Chinese Patent Application No. 201510552566.X.
Communication dated Apr. 3, 2017 by the European Patent Office in counterpart European Patent Application No. 15172774.0.
Search Report dated May 20, 2014, issued by the International Searching Authority in related International Application No. PCT/KR2014/001848.
Written Opinion dated May 20, 2014, issued by the International Searching Authority in related International Application No. PCT/KR2014/001848.
Communication dated Jul. 17, 2014, issued by the European Patent Office in related European Application No. 14159249.3.
Office Action dated Jul. 29, 2014 in Parent U.S. Appl. No. 14/205,762.
Final Office Action dated Jan. 15, 2015 in Parent U.S. Appl. No. 14/205,762.
KIPO Translation of KR 10 2012 0036420, accessed online Jan. 6, 2015.
Google Translation of CN 102793565, accessed online Jan. 6, 2015.
Communication dated May 16, 2018, from the European Patent Office in counterpart European Application No. 18155774.5.
Communication dated Feb. 21, 2018, from the European Patent Office in counterpart European Application No. 15172774.0.
Communication dated Apr. 2, 2018, from the State Intellectual Property Office of People's Republic of China in counterpart Application No. 201510552566.X.
Communication dated Sep. 27, 2018, issued by the European Patent Office in counterpart European Application No. 15172774.0.
Communication dated Mar. 22, 2017, issued by the United States Patent and Trademark Office in related U.S. Appl. No. 14/205,762.
Communication dated Apr. 18, 2017, issued by the United Stales Patent and Trademark Office in related U.S. Appl. No. 14/205,762.
Communication dated Sep. 26, 2017, issued by the United Stales Patent and Trademark Office in related U.S. Appl. No. 14/205,762.
Communication dated Apr. 5, 2018, issued by the United States Patent and Trademark Office in related U.S. Appl. No. 14/205,762.
Communication dated Oct. 12, 2018, issued by the United Slates Patent and Trademark Office in related U.S. Appl. No. 14/205,762.
Communication dated Jan. 10, 2019, issued by the United Slates Patent and Trademark Office in related U.S. Appl. No. 14/205,762.
Communication dated Nov. 30, 2017, issued by the United States Patent and Trademark Office in related U.S. Appl. No. 14/521,627.
Communication dated Apr. 2, 2018, issued by the United States Patent and Trademark Office in related U.S. Appl. No. 14/521,627.
Communication dated Nov. 15, 2018, issued by the United States Patent and Trademark Office in related U.S. Appl. No. 14/521,627.
Communication dated Mar. 13. 2019, issued by the United States Patent and Trademark Office in related U.S. Appl. No. 14/521,627.
Communication dated Jul. 31, 2015, issued by the United States Patent and Trademark Office in related U.S. Appl. No. 14/582,415.
Communication dated Jan. 29, 2016, issued by the United States Patent and Trademark Office in related U.S. Appl. No. 14/582,415.
Communication dated Mar. 20, 2017, issued by the United States Patent and Trademark Office in related U.S. Appl. No. 14/582,415.
Communication dated Oct. 12, 2017, issued by the United States Patent and Trademark Office in related U.S. Appl. No. 14/582,415.
Communication dated Mar. 7, 2018, issued by the United States Patent and Trademark Office in related U.S. Appl. No. 14/582,415.
Communication dated Aug. 16, 2018, issued by the United States Patent and Trademark Office in related U.S. Appl. No. 14/582,415.
Communication dated Mar. 5, 2019, issued by the United States Patent and Trademark Office in related U.S. Appl. No. 14/582,415.
Decision to Grant dated Jul. 13, 2017 in EP 15191427.2.
"SMART Board—Level 1—3e—Manipulation Objects—Infinite Cloner", YouTube Video Published 2-29/201 at httsp://www.youtube.com/watch?v=RPRE_2J9YA.
Communication dated May 17, 2019, issued by the Chinese Patent Office in counterpart Chinese Application No. 201510552566.X.
Communication dated Mar. 1, 2019, issued by the State Intellectual Property Office of P.R. China in counterpart Chinese Application No. 201510552566.X.
Communication dated Nov. 27, 2019, issued by the United States Patent and Trademark Office in counterpart U.S. Appl. No. 14/582,415.
Communication dated Mar. 5, 2020 issued by the Chinese Patent Office in counterpart Chinese Application No. 201510552566.X, total of 27 pages with translation.
Communication dated Nov. 4, 2019 issued by the State Intellectual Property Office of P.R. China in counterpart Chinese Application No. 201510552566.X.
Communication dated Dec. 10, 2019 issued by the Indian Intellectual Property Office in Indian counterpart Application No. 2752/MUMNP/2015.
Communication dated Apr. 16, 2020 issued by the United States Patent and Trademark Office in counterpart U.S. Appl. No. 15/375,444.
Communication dated May 20, 2020, issued by the State Intellectual Property Office of P.R. China in counterpart Chinese Application No. 201510552566.X.
Communication dated Aug. 10, 2020 issued by the State Intellectual Property Office of P.R. China in counterpart Chinese Application No. 201510552566.X.

* cited by examiner

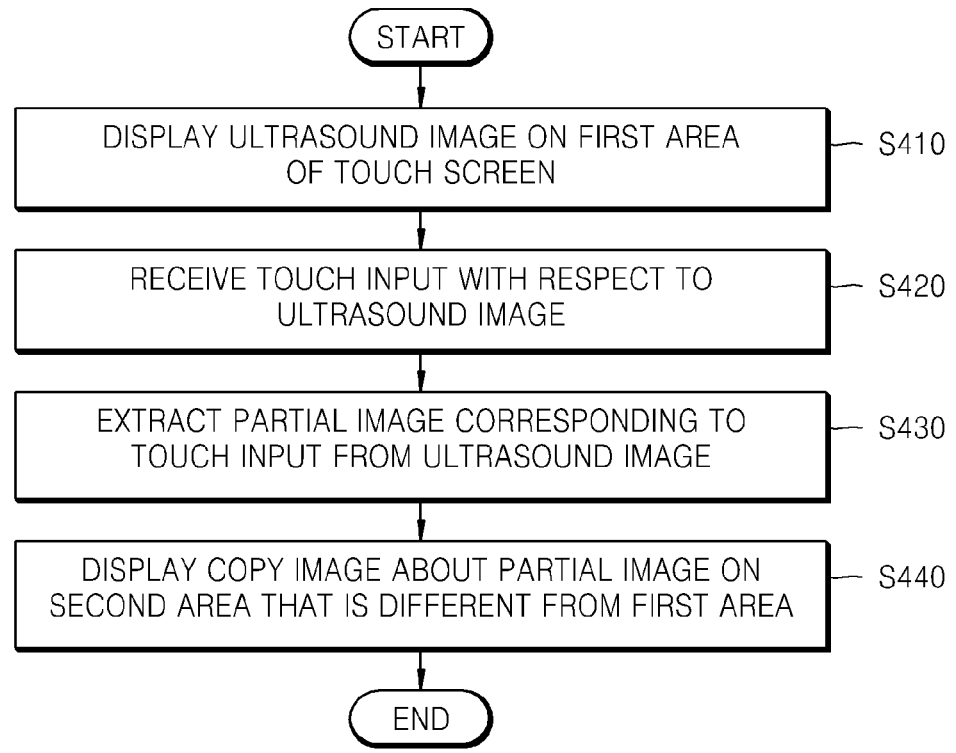
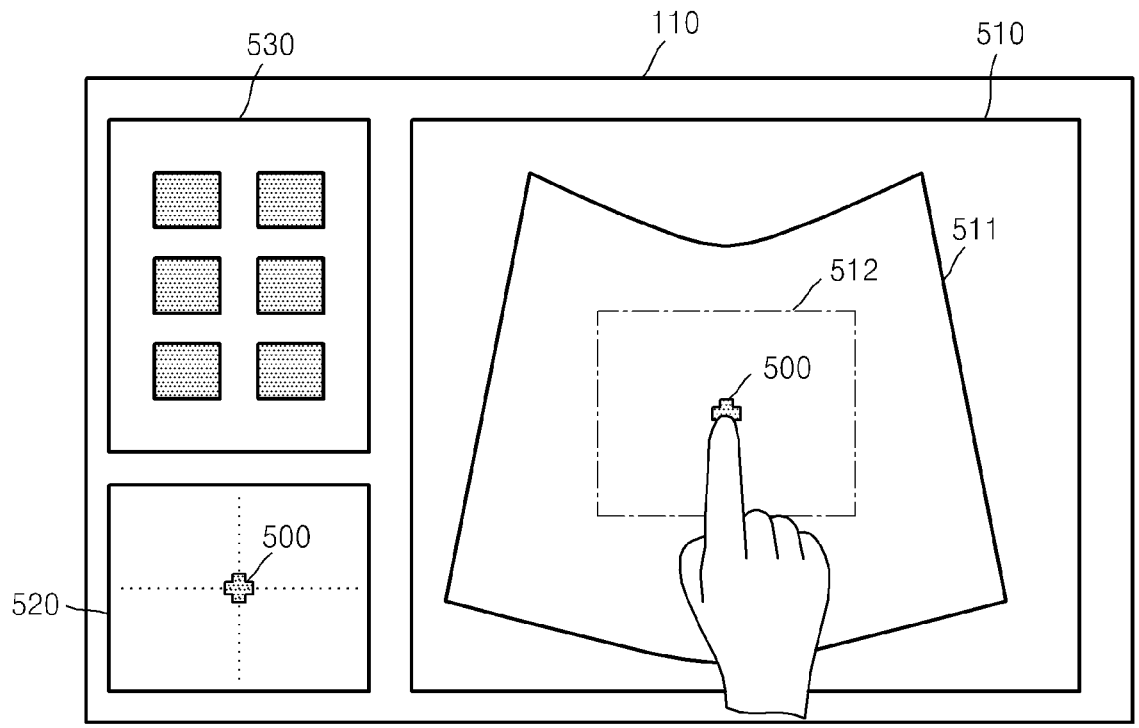

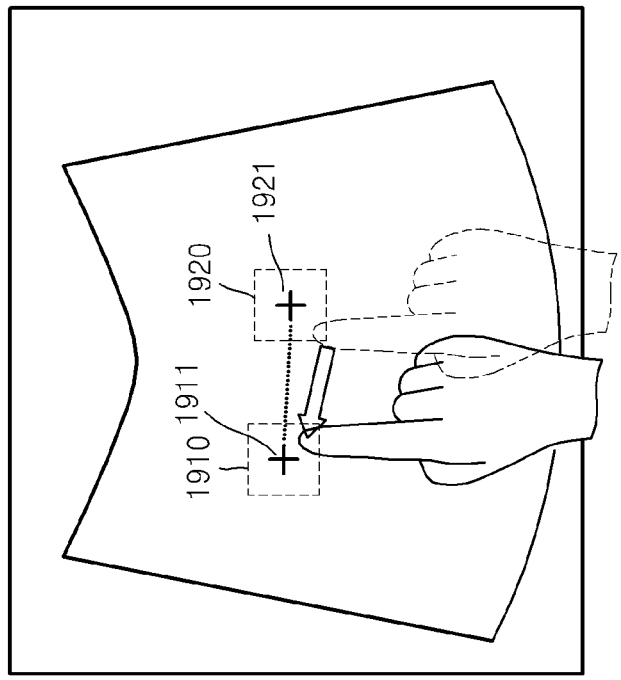
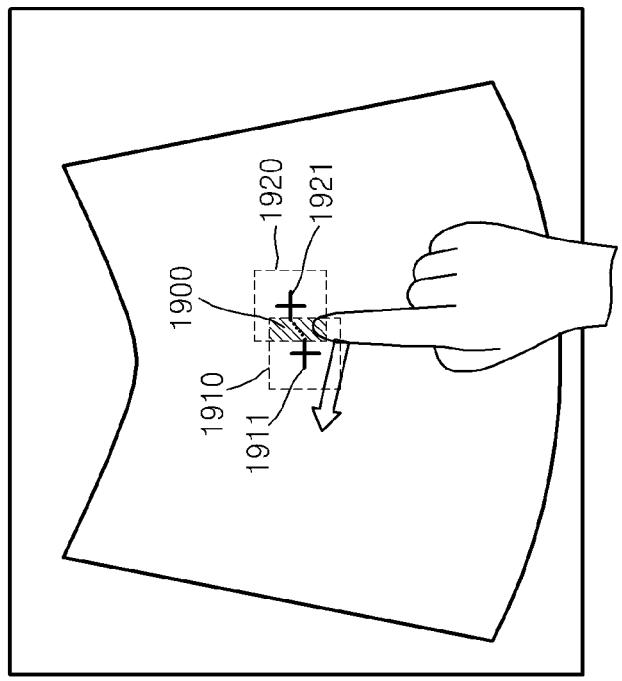

METHOD OF PROVIDING COPY IMAGE AND ULTRASOUND APPARATUS THEREFOR

CROSS-REFERENCE TO RELATED PATENT APPLICATIONS

This application is a continuation application of U.S. patent application Ser. No. 14/205,762 filed Mar. 12, 2014, which claims the benefit of U.S. Provisional Patent Application No. 61/779,520, filed Mar. 13, 2013, and claims priority from Korean Patent Application Nos. 10-2013-0040025, filed Apr. 11, 2013, and 10-2013-0067943, filed Jun. 13, 2013 in the Korean Intellectual Property Office. The disclosures of all of the above applications are incorporated herein by reference in their entireties.

BACKGROUND

1. Field

The present disclosure relates to a method of providing a copy image and an ultrasound apparatus therefor.

2. Description of the Related Art

An ultrasound diagnostic apparatus transmits an ultrasound signal from a body surface to a predetermined part inside a human body, and obtains an image of a cross-section of or a blood flow in a soft tissue by using information of the reflected ultrasound signal.

The ultrasound diagnostic apparatus is advantageous in that the ultrasound diagnostic apparatus is small, inexpensive, and capable of displaying an image in real-time. Also, the ultrasound diagnostic apparatus is safe without a risk of radioactivity due to an X-ray or the like, such that the ultrasound diagnostic apparatus may be widely used with other image diagnostic apparatuses such as an X-ray diagnostic apparatus, a computed tomography (CT) scanner, a magnetic resonance imaging (MRI) apparatus, a nuclear medicine diagnostic apparatus, or the like.

Values that are measured by using the ultrasound diagnostic apparatus are highly related to a lesion diagnosis or the like, and thus the values have to be exact. Thus, apparatuses and methods are needed to allow a user to exactly select a measurement portion. Also, apparatuses and methods are needed to allow a user who uses a touch interface to freely adjust a length and position of a measurement line.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more of exemplary embodiments provide a method of providing a copy image and an ultrasound apparatus therefor, whereby the copy image of a part that is obstructed by a touch instrument (such as a finger, an electronic pen, or the like) is separately provided at a predetermined area, thus, a user may exactly select a measurement portion or a selection portion of an ultrasound image.

According to an aspect of an exemplary embodiment, there is provided a method of providing a copy image, the method including operations of displaying an ultrasound image on a first area of a touch screen; receiving a touch input with respect to the ultrasound image; extracting a partial image corresponding to the touch input from the ultrasound image; and displaying a copy image of the partial image on a second area that is different from the first area on which the ultrasound image is displayed.

The operation of extracting the partial image may include operations of obtaining information about a position on the touch screen at which the touch input is received; and extracting a copy image having a preset size with respect to the position.

The operation of displaying the copy image may include operations of capturing the partial image corresponding to the touch input; and displaying the captured partial image as the copy image on the second area.

The operation of displaying the copy image may be performed so that an object that is displayed at a position on the touch screen at which the touch input is received may be located at a center of the second area.

The object may include at least one of a reference point for selection of a measurement portion or a measurement area, a sample volume, a body marker, an arrow, and an annotation.

The method may further include an operation of displaying a plurality of objects on the first area, wherein each of the plurality of objects is activated to be moved according to the touch input.

The operation of displaying the copy image may include operations of changing a control panel for adjustment of a parameter value related to the ultrasound image, according to a predetermined mode, and then displaying the changed control panel on a third area of the touch screen; selecting the second area that is different from the first area and the third area; and displaying the copy image on the second area.

The predetermined mode may include at least one of a brightness mode (B mode), a Doppler mode, and a motion mode (M mode).

The operation of displaying the copy image may include operations of receiving a drag input that starts at a position on the touch screen at which the touch input is received; and displaying the copy image of the partial image on the second area, wherein the partial image is changed according to the drag input.

The operation of displaying the copy image may include an operation of moving an object, which is displayed at a position on the touch screen at which the touch input is received, according to the drag input and then displaying the object on the first area.

The operation of receiving the touch input may include an operation of receiving multiple touch inputs with respect to at least two portions of the ultrasound image, and the operation of displaying the copy image may include an operation of displaying a plurality of copy images about a plurality of partial images on the second area, wherein the plurality of partial images correspond to the at least two portions, respectively.

The operation of displaying the copy image may include an operation of displaying the copy image on the second area, wherein the copy image is magnified or reduced by a predetermined ratio.

When the touch input is no longer received, the method may further include an operation of removing the copy image from the second area.

The second area does not overlap with the first area on which the ultrasound image is displayed.

The second area may include a residual area of the first area on which the ultrasound image is displayed, wherein the residual area excludes an interest area that is selected by a user.

According to an aspect of an exemplary embodiment, there is provided an ultrasound apparatus including a display for displaying an ultrasound image on a first area of a touch screen; a user input unit for receiving a touch input with respect to the ultrasound image; and a controller for extracting a partial image corresponding to the touch input from the ultrasound image, and for controlling the display to display a copy image of the partial image on a second area that is different from the first area on which the ultrasound image is displayed.

The controller may obtain information about a position on the touch screen at which the touch input is received, and may extract a copy image having a preset size with respect to the position.

The ultrasound apparatus may further include an image processor for generating the copy image by capturing the partial image corresponding to the touch input.

The display may display the copy image so that an object that is displayed at a position at which the touch input is received may be located at a center of the second area.

The display may further display a plurality of objects on the first area, wherein each of the plurality of objects is activated to be moved according to the touch input.

The display may change a control panel for adjustment of a parameter value related to the ultrasound image, according to a predetermined mode, and then may display the control panel on a third area of the touch screen, and the controller may select the second area that is different from the first area and the third area.

The user input unit may receive a drag input that starts at a position (at which the touch input is received, and the display may display the copy image of the partial image on the second area, wherein the partial image is changed according to the drag input.

The user input unit may receive multiple touch inputs with respect to at least two portions of the ultrasound image, and the display may display a plurality of copy images about a plurality of partial images on the second area, wherein the plurality of partial images correspond to the at least two portions, respectively.

The display may display the copy image on the second area, wherein the copy image is magnified or reduced by a predetermined ratio.

When the touch input is no longer received, the display may remove the copy image from the second area.

According to an aspect of an exemplary embodiment, there is provided a method of providing a copy image, the method including operations of outputting an ultrasound signal to a target via a probe, and receiving an ultrasound response signal from the target; generating an ultrasound image about the target base on the ultrasound response signal; displaying the ultrasound image about the target on a first area of a touch screen; receiving a touch input by a user with respect to the ultrasound image; and displaying a copy image of a partial image on a second area that is different from the first area on which the ultrasound image is displayed, wherein the partial image corresponds to the touch input.

The ultrasound image about the target may be changed according to a position or an angle of the probe.

According to an aspect of an exemplary embodiment, there is provided a method of providing a copy image, the method including operations of displaying a body marker including a target figure and a probe figure on a first area of a touch screen; receiving a touch input by a user with respect to the body marker; and displaying a copy image of the body marker on a second area that is different from the first area, based on the touch input.

The operation of displaying the copy image may be performed so that the target figure may be located at a center of the second area.

The method may further include operations of receiving a drag input that involves moving the probe figure displayed on the first area; moving a position of the probe figure, based on the drag input; and displaying a body marker including the target figure and the moved probe figure on the first area.

The method may further include an operation of displaying a changed copy image, which is changed according to the drag input, on the second area.

The operation of displaying the changed copy image may include an operation of displaying a copy image of the body marker including the target figure and the moved probe figure on the second area.

One or more of exemplary embodiments provide a method and an ultrasound apparatus for displaying a plurality of objects related to an ultrasound image by activating the plurality of objects, whereby each of the plurality of objects may be moved according to a user's touch input.

One or more of exemplary embodiments provide a method and an ultrasound apparatus for displaying an object by expanding a touch recognition range of the object, whereby, when a user exactly touches an object by using a touch instrument (e.g., a finger or an electronic pen) but the object is obstructed by the touch instrument, the user may move the object although the user touches an area around the object.

One or more of exemplary embodiments provide a method and an ultrasound apparatus for displaying a plurality of objects, whereby, when touch recognition ranges of the plurality of objects overlap with each other, a movement order of the plurality of objects is determined according to priority orders.

The method may include operations of extracting the plurality of objects that are movable during a predetermined mode; activating the plurality of objects to allow each of the plurality of objects to be moved according to a user's touch input; and displaying together the plurality of activated objects and an ultrasound image.

Each of the plurality of activated objects may include at least one of a reference point, a reference line, annotation, and an arrow which are used in selecting a measurement point or a measurement area.

The method may further include operations of receiving a touch and drag input with respect to at least one object from among the plurality of activated objects; and moving and displaying the at least one object according to the touch and drag input.

The operation of moving and displaying may include operations of receiving a touch and drag input with respect to a first area within a predetermined radius from a point at which a first object from among the plurality of activated objects is displayed; moving and displaying the first object according to the touch and drag input with respect to the first area; receiving a touch and drag input with respect to a second area within the predetermined radius from a point at which a second object from among the plurality of activated objects is displayed; and moving and displaying the second object according to the touch and drag input with respect to the second area.

The method may further include operations of receiving a touch and drag input with respect to an area in which the first area and the second area overlap with each other; and moving and displaying at least one of the first object and the second object, based on priority order information.

The operation of moving and displaying at least one of the first object and the second object may include operations of comparing movement time information of the first object with movement time information of the second object; and move and displaying one of the first object and the second object according to a result of the comparing.

The method may further include operations of receiving multiple touch inputs with respect to the first object and the second object included in the plurality of activated objects; and moving and displaying the first object and the second object, respectively, according to the multiple touch inputs.

The ultrasound image may include at least one of a B mode image, Doppler image, an M mode image, and an elasticity mode image.

The ultrasound apparatus may include a user input unit for receiving a user's touch input; a controller for extracting the plurality of objects that are movable during a predetermined mode, and activating the plurality of objects to allow each of the plurality of objects to be moved according to the user's touch input; and a display for displaying together the plurality of activated objects and an ultrasound image.

The user input unit may receive a touch and drag input with respect to at least one object from among the plurality of activated objects, and the display may move and display the at least one object according to the touch and drag input.

The user input unit may receive a touch and drag input with respect to a first area within a predetermined radius from a point at which a first object from among the plurality of activated objects is displayed, and may receive a touch and drag input with respect to a second area within the predetermined radius from a point at which a second object from among the plurality of activated objects is displayed, and the display may move and display the first object according to the touch and drag input with respect to the first area, and may move and display the second object according to the touch and drag input with respect to the second area.

The user input unit may receive a touch and drag input with respect to an area in which the first area and the second area overlap with each other, and the controller may control the display to move and to display at least one of the first object and the second object, based on priority order information.

The controller may compare movement time information of the first object with movement time information of the second object, and may move and display one of the first object and the second object according to a result of the comparison.

The user input unit may receive multiple touch inputs with respect to the first object and the second object included in the plurality of activated objects, and the display may move and display the first object and the second object, respectively, according to the multiple touch inputs.

According to an aspect of an exemplary embodiment, there is provided a method of providing an ultrasound image, the method including operations of dividing a touch screen into a first area and a second area, to be separate from and non-overlapping with the first area and of a smaller size than that of the first area; displaying the ultrasound image on the first area of a touch screen; receiving a touch input at a touch position, from the first area; extracting a partial image including a smaller portion of the ultrasound image containing the touch position, from the ultrasound image; and displaying a copy image of the partial image on the second area, while contemporaneously displaying an entire ultrasound image on the first area.

The touch position may correspond to an object of the ultrasound image displayed on the first area and the operation of extracting may include operations of obtaining positional information of the touch position on the first area; extracting the smaller portion of the ultrasound image having a preset size and surrounding the touch position; and displaying the object in a center of the copy image on the second area.

The touch position may correspond to a first object of the ultrasound image displayed on the first area and the operation of displaying may include displaying other objects of the ultrasound image on the first area, the first object and all or some of the other objects may be activated to be movable according to the touch input.

The operation of displaying the copy image may include magnifying the copy image of the partial image, on the second area.

BRIEF DESCRIPTION OF THE DRAWINGS

The above and/or other aspects will become more apparent by describing certain exemplary embodiments, with reference to the accompanying drawings, in which:

FIG. 4 is a flowchart illustrating a method of providing a copy image, according to an exemplary embodiment;

FIGS. 5A and 5B illustrate a display of the ultrasound apparatus, according to an exemplary embodiment;

FIGS. 19A and 19B illustrate cases in which touch recognition ranges of objects overlap with each other, according to an exemplary embodiment;

DETAILED DESCRIPTION

Figure 1:
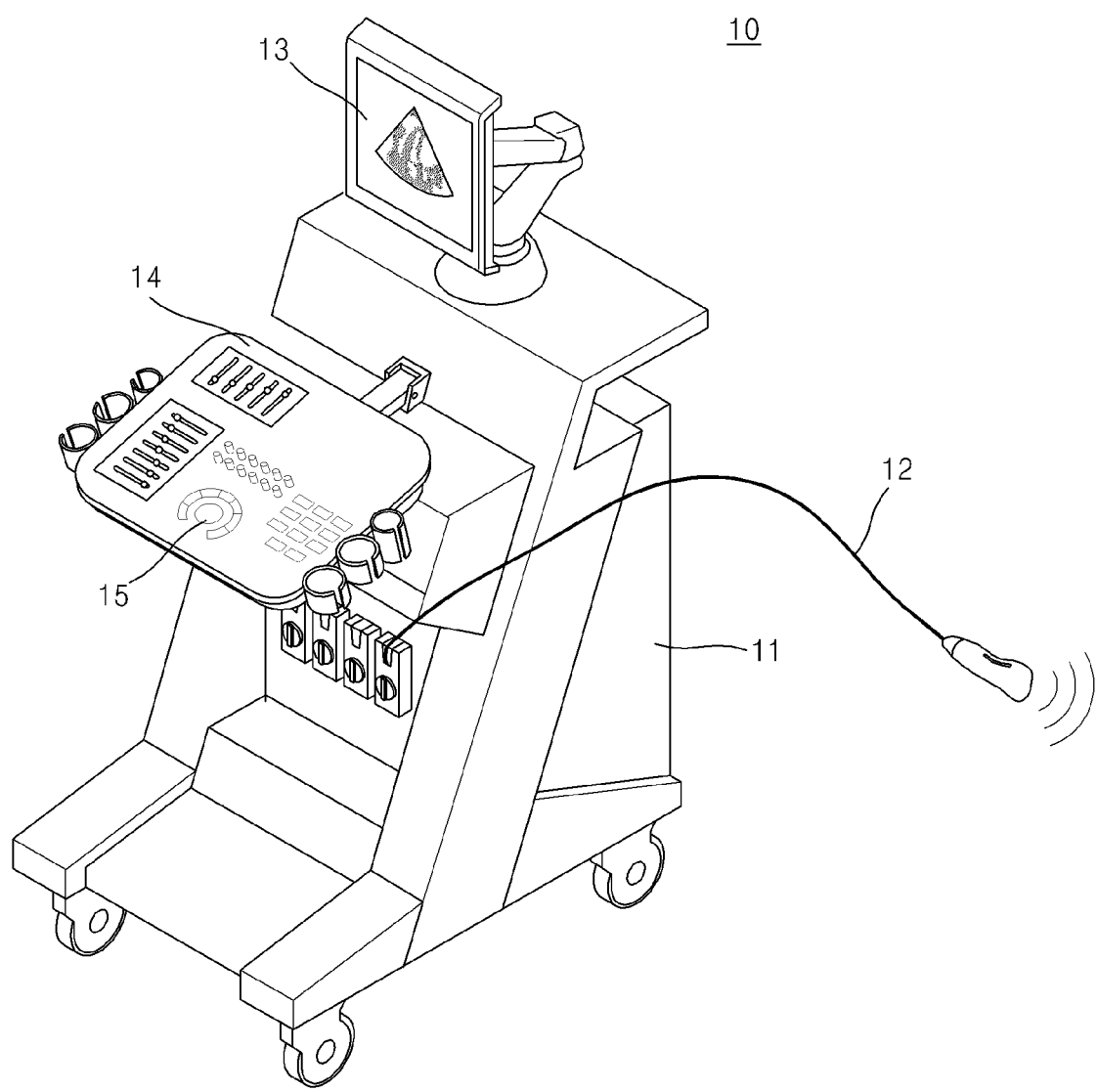
FIG. 1 illustrates a related art ultrasound apparatus.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described with reference to exemplary embodiments. Thus, the terms used herein have to be defined based on the meaning of the terms together with the description throughout the specification.

Also, when a part "includes" or "comprises" an element, unless there is a particular description contrary thereto, the part can further include other elements, not excluding the other elements. In the following description, terms such as "unit" and "module" indicate a unit for processing at least one function or operation, wherein the unit and the block may be embodied as hardware or software or embodied by combining hardware and software.

Throughout the specification, "ultrasound image" indicates an image of a target object which is obtained by using an ultrasound signal. The target object may be a part of a human body. For example, the target object may include organs such as the liver, the heart, the nuchal translucency (NT), the brain, the breast, the abdominal region, or the like, or a fetus.

The ultrasound image may vary in different forms. For example, the ultrasound image may be, but is not limited to, at least one of an image obtained during a brightness mode (hereinafter, referred to as "B mode image") indicating brightness as magnitude of an ultrasound echo signal that is reflected from the target, an image obtained during a color mode (hereinafter, referred to as "C mode image") indicating a color as speed of a moving target by using a Doppler effect, an image obtained during a Doppler mode (hereinafter, referred to as "D mode image") indicating a spectrum image of a moving target by using a Doppler effect, an image obtained during a motion mode (hereinafter, referred to as "M mode image") indicating motion of a target at a predetermined position according to time, and an image obtained during an elasticity mode (hereinafter, referred to as "elasticity mode image) indicating a difference between a reaction when compression is applied to a target and a reaction when compression is not applied to the target. Also, in one or more exemplary embodiments, the ultrasound image may be a two-dimensional (2D) image, a three-dimensional (3D) image, or a four-dimensional (4D) image.

Throughout the specification, a "user" may be a medical expert including a doctor, a nurse, a medical laboratory technologist, a sonographer, or the like.

Throughout the specification, the expression "an object is activated" means that the object may be movable according to a user's touch input.

Expressions such as "at least one of," when preceding a list of elements, modify the entire list of elements and do not modify the individual elements of the list.

FIG. 1 illustrates a related art ultrasound apparatus 10.

As illustrated in FIG. 1, the related art ultrasound apparatus 10 includes a main body 11, at least one probe 12, a display 13, and a control panel 14. Since the related art ultrasound apparatus 10 has a large size, it is difficult for a user to freely move the related art ultrasound apparatus 10 to different places. Also, due to its large size, the related art ultrasound apparatus 10 occupies a large space.

The display 13 and the control panel 14 of the related art ultrasound apparatus 10 are separated. Thus, when the user selects or measures a predetermined area of an ultrasound image or adjusts a gain of the ultrasound image that is obtained by using the at least one probe 12, the user has to check the ultrasound image and operate the control panel 14 in turn, such that a view of the user may be distracted.

Also, the user of the related art ultrasound apparatus 10 may move an object displayed on the display 13, by using a track ball 15 included in the control panel 14. Here, when the user attempts to move another object, the user has to additionally map the track ball 15 with the other object, such that it is difficult for the user to rapidly change a measurement point or a measurement line. This is described below with reference to FIGS. 2A and 2B.

Figure 2A:
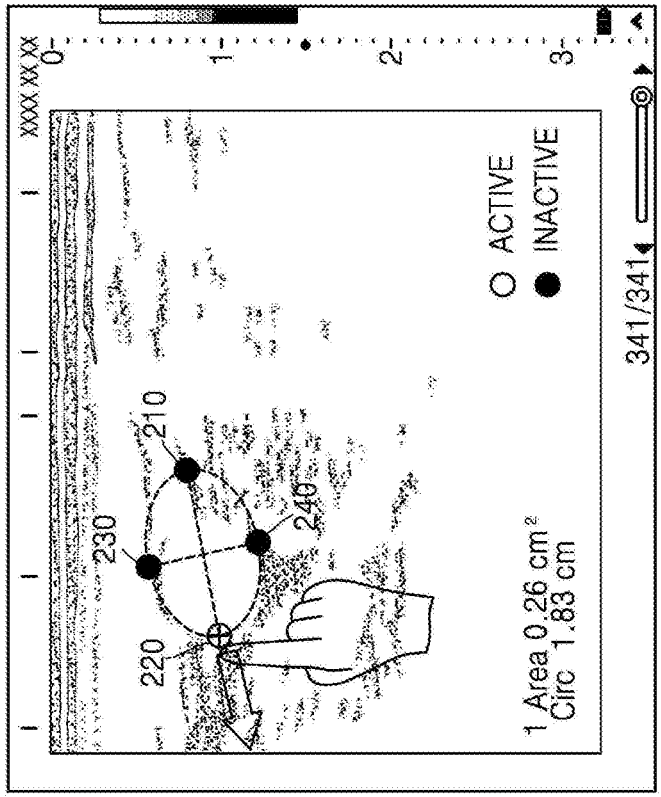
FIGS. 2A and 2B illustrate objects provided by the related art ultrasound apparatus.
Figure 2B:
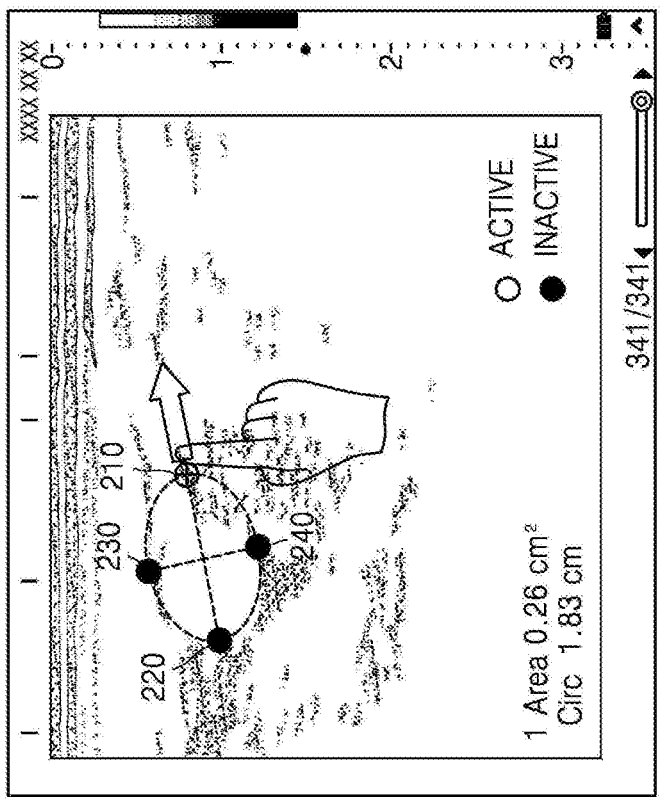

FIGS. 2A and 2B illustrate objects provided by the related art ultrasound apparatus 10.

As illustrated in FIG. 2A, the related art ultrasound apparatus 10 may activate motion with respect to only one object. That is, when a first object 210 is activated, a user may move only the first object 210 by using a track ball, a mouse, or a touch instrument (e.g., a finger or an electronic pen), and cannot move a second object 220, a third object 230, and a fourth object 240.

Thus, as illustrated in FIG. 2B, when the user attempts to move the second object 220, the related art ultrasound apparatus 10 has to change an activated position from the first object 210 to the second object 220. That is, the related art ultrasound apparatus 10 has to inactivate the activated first object 210 and to activate the second object 220 into an activated state. Thus, it is difficult for the user to rapidly move each of a plurality of objects.

Also, as illustrated in FIGS. 2A and 2B, when the user touches an object by using the touch instrument (e.g., the finger or the electronic pen), the object is obstructed by the touch instrument. Thus, it is difficult for the user to exactly move the object to a target position.

Figure 3:
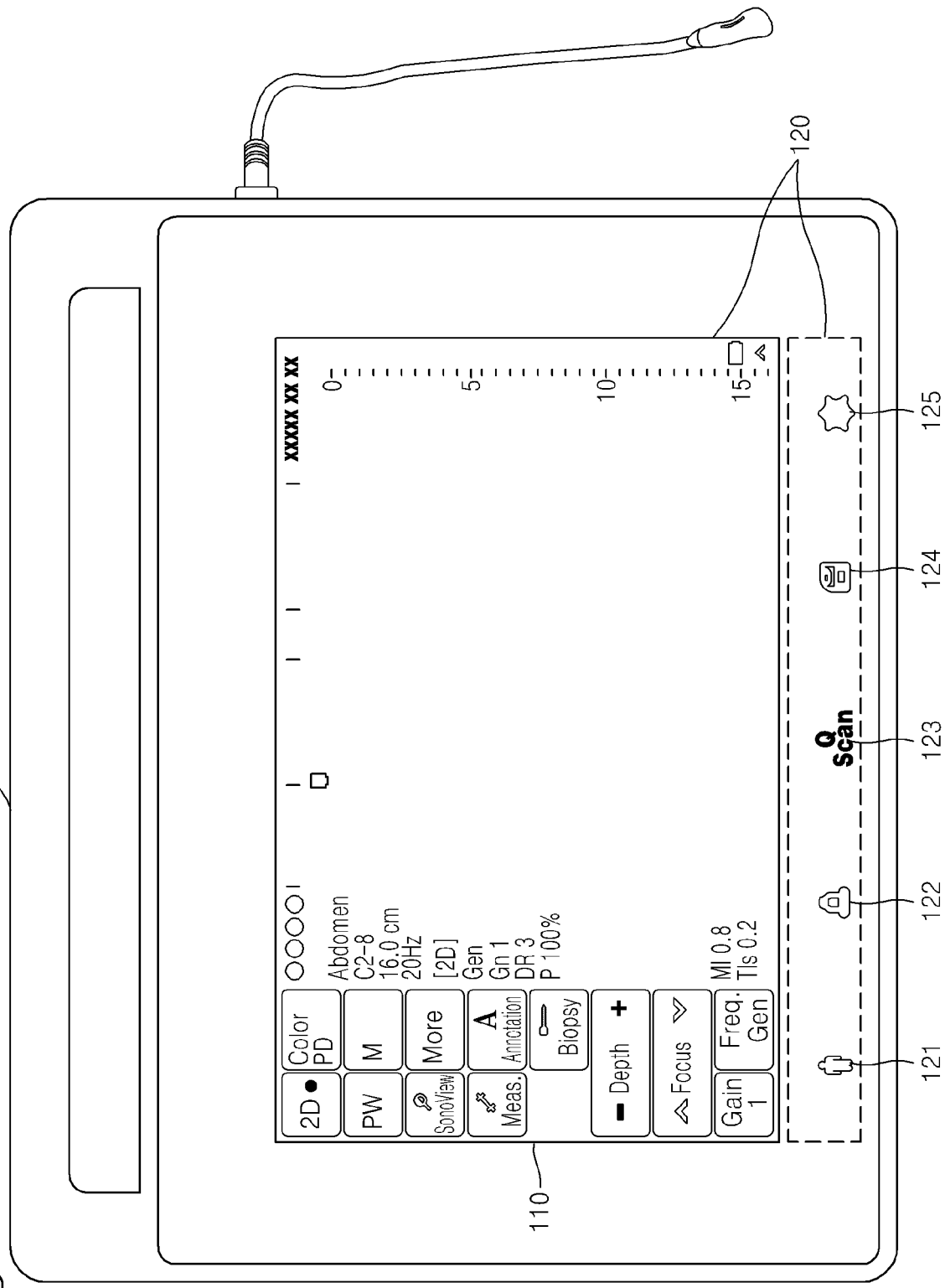
FIG. 3 illustrates an ultrasound apparatus according to an exemplary embodiment.

FIG. 3 illustrates an ultrasound apparatus 100 according to an exemplary embodiment.

As illustrated in FIG. 3, the ultrasound apparatus 100 may include a display 110, a user input unit 120, and an interface to connect a probe.

In the present exemplary embodiment, the display 110 and a touchpad may form a mutual layer structure and thus may be formed as a touch screen. In the present exemplary embodiment, the display 110 may be used as both an output device and an input device.

The touch screen may receive a touch input position and a touched area and may also receive a touch input pressure. The touch screen may receive an actual touch and/or may receive a proximate touch.

In an exemplary embodiment, the term "actual touch" indicates a case in which a pointer actually touches a screen, and the term "proximate touch" indicates a case in which a pointer does not actually touch a screen but approaches the screen within a predetermined distance. In an exemplary embodiment, the pointer indicates an instrument that is used to touch or to proximately touch a specific portion of a displayed screen. Examples of the pointer include an electronic pen, a finger, and the like.

Although not illustrated, in order to recognize an actual touch or a proximate touch on the touch screen, the ultrasound apparatus 100 may internally or externally have various sensors in the touch screen. An example of the sensor to receive the touch on the touch screen may include a tactile sensor.

The tactile sensor detects a contact of a specific object at least as much as a person can detect. The tactile sensor may detect various types of information such as roughness of a contact surface, hardness of the contact object, temperature of a contact point, or the like.

Another example of the sensor for detecting the touch on the touch screen may include a proximity sensor. The proximity sensor detects existence of an object that approaches a predetermined detection surface or that exists nearby, by using a force of an electro-magnetic field or an infrared ray, without using a mechanical contact.

Examples of the proximity sensor include a transmission-type photoelectric sensor, a direction reflection-type photoelectric sensor, a mirror reflection-type photoelectric sensor, a high frequency oscillation-type proximity sensor, a capacity-type proximity sensor, a magnetic proximity sensor, an infrared-type proximity sensor, or the like.

The display 110 may include, but is not limited thereto, at least one of a liquid crystal display (LCD), a thin film transistor-liquid crystal display (TFT-LCD), an organic light-emitting display device, a flexible display, and a 3D display.

In the present exemplary embodiment, the display 110 may provide a copy image corresponding to a touch input portion by a user, so that the display 110 may allow the user to select an exact portion of the ultrasound image. This will be described in detail with reference to FIG. 4.

The display 110 may display a plurality of activated objects. This will be described in detail with reference to FIG. 7.

The user input unit 120 is a means by which the user inputs data to control the ultrasound apparatus 100. The user input unit 120 may include a touchpad (a touch capacitive type touchpad, a pressure resistive type touchpad, an infrared beam sensing type touchpad, a surface acoustic wave type touchpad, an integral strain gauge type touchpad, a Piezo effect type touchpad, or the like), a key pad, or the like. In particular, as described above, the touchpad and the display 110 may form the mutual layer structure and thus may be formed as the touch screen.

In the present exemplary embodiment, the ultrasound apparatus 100 may display an ultrasound image during a predetermined mode and a control panel about the ultrasound image on the touch screen. Then, the ultrasound apparatus 100 may detect a touch gesture by the user to the ultrasound image via the touch screen.

Throughout the specification, the touch gesture (i.e., the touch input) by the user may include a tap gesture, a touch and hold gesture, a double tap gesture, a drag gesture, a panning gesture, a flick gesture, a drag and drop gesture, a swipe gesture, a pinch gesture, or the like.

The "tap gesture" indicates a case in which the user touches the touch screen by using a finger or an electronic pen and then instantly takes away the finger or the electronic pen from the touch screen without moving the finger or the electronic pen on the touch screen.

The "touch and hold gesture" indicates a case in which the user touches the touch screen by using a finger or an electronic pen and maintains a touch input for at least a threshold time (e.g., 2 seconds). That is, a time interval between a touch-in time and a touch-out time is equal to or greater than the threshold time (e.g., 2 seconds). In order to allow the user to recognize whether a touch input is the tap gesture or the touch and hold gesture, if the touch input is maintained for at least a threshold time, a feedback signal may be provided in a visual, acoustic, or tactile manner. The threshold time may vary in one or more exemplary embodiments.

The "double tap gesture" indicates a case in which the user touches the touch screen twice by using a finger or an electronic pen.

The "drag gesture" indicates a case in which the user touches the touch screen by using a finger or an electronic pen and then moves the finger or the electronic pen to another position on the touch screen while the user maintains the touch. Due to the drag gesture, an object is moved or the panning gesture to be described below is performed.

The "panning gesture" indicates a case in which the user performs the drag gesture without selecting an object. The panning gesture does not select a particular object, so that an object is not moved within a page but a page itself may be moved within a screen or an object group is moved within the page.

The "flick gesture" indicates a case in which the user performs a drag gesture by using a finger or an electronic pen at a speed equal to or greater than a threshold speed (e.g., 100 pixel/second). Based on whether a movement speed of the finger or the electronic pen is equal to or greater than the threshold speed (e.g., 100 pixel/second), the drag gesture (or the panning gesture) and the flick gesture may be distinguished.

The "drag and drop gesture" indicates a case in which the user drags an object to a predetermined position in a screen, by using a finger or an electronic pen, and then takes away the finger or the electronic pen from the touch screen.

The "pinch gesture" indicates a case in which the user touches the touch screen by using two fingers and then moves the two fingers in different directions. The pinch gesture is for a pinch open or a pinch close with respect to an object or a page, and a value of the pinch open or a value of the pinch close is determined according to a distance between the two fingers.

The "swipe gesture" indicates a case in which the user touches an object in a screen by using a finger or an electronic pen, and horizontally or vertically moves the object by a predetermined distance. A movement in a diagonal direction is not detected as the swipe gesture.

The ultrasound apparatus 100 may physically include some buttons that are frequently used by the user and that are included in the control panel of the related art ultrasound apparatus, and may provide the as a graphical user interface (GUI) via the touch screen.

For example, the user input unit 120 may physically include, but is not limited thereto, a patient button 121, a probe button 122, a scan button 123, a storage button 124, an ultrasound image selection button 125, or the like.

The patient button 121 involves selecting a patient who undergoes an ultrasound diagnosis. The probe button 122 involves selecting a probe to be used in the ultrasound diagnosis. The scan button 123 involves quickly compensating for an ultrasound image by using a parameter value that is preset in the ultrasound apparatus 100. The storage button 124 involves storing an ultrasound image. The ultrasound image selection button 125 involves pausing ultrasound images that are displayed in real-time and then allowing one paused ultrasound image to be displayed on a screen.

The user input unit 120 may include, but is not limited thereto, a 2D button, a color button, a PW button, an M button, a SonoView button (i.e., a button for checking pre-stored images), a More button, a Meas. button (i.e., a measure button), an Annotation button, a Biopsy button (i.e., a button for guiding an insertion position for a needle), a Depth button, a Focus button, a Gain button, a Freq. button (i.e., frequency button), or the like as the GUI. A function of each of the aforementioned buttons may be easily derived by one of ordinary skill in the ultrasound art in view of names of the buttons, thus, detailed descriptions for the buttons are omitted here.

Hereinafter, a method of providing a copy image is described in detail with reference to FIG. 4, wherein the ultrasound apparatus 100 having a touch screen performs the method to help a user to perform an exact touch input on an ultrasound image that is displayed via the touch screen.

FIG. 4 is a flowchart illustrating a method of providing a copy image, performed by the ultrasound apparatus 100, according to an exemplary embodiment.

In operation S410, the ultrasound apparatus 100 may display an ultrasound image on a first area of a touch screen. According to the present exemplary embodiment, the ultrasound image may be, but is not limited to, one of a B mode image, a Doppler image, an M mode image, and a C mode image.

The ultrasound apparatus 100 may display a plurality of ultrasound images on the first area of the touch screen. For example, the ultrasound apparatus 100 may display the B mode image and the Doppler image on the first area or may display the B mode image and the M mode image on the first area.

The ultrasound apparatus 100 may display a predetermined object on the ultrasound image, based on user setting. For example, the ultrasound apparatus 100 may display a reference line or a reference point with respect to selection of a region of interest (ROI), a body marker, or a sample volume on the ultrasound image.

According to the present exemplary embodiment, the body marker may be a figure that represents a position or a target, which is scanned by ultrasound. The body marker may include a figure indicating an ultrasound-scanned target, and a figure corresponding to a position of a probe that contacts the target. Examples of the body marker may include an arm figure, a liver figure, a womb figure, or the like.

According to the present exemplary embodiment, the sample volume indicates a limited zone in which a Doppler signal is input due to an operation of a range gate.

The ultrasound apparatus 100 may adjust a size of the sample volume by varying a size of the range gate. When the size of the range gate is increased, the sample volume involving the obtaining of the Doppler signal is also increased. According to the present exemplary embodiment, the user may obtain a Doppler image at a specific position, by moving a position of the sample volume.

In operation S420, the ultrasound apparatus 100 may detect a touch input to the ultrasound image. According to the present exemplary embodiment, the ultrasound apparatus 100 may obtain information about a position of the touch screen at which the touch input is detected. The information about the position at which the touch input is detected may include a coordinate value (e.g., a pixel value) of the position of the touch screen at which the touch input is detected.

The touch input may include a touch and hold gesture, a drag gesture, a swipe gesture, or the like. The ultrasound apparatus 100 may detect multiple touch inputs with respect to at least two portions of the ultrasound image. For example, the ultrasound apparatus 100 may detect a pinch gesture by the user.

In operation S430, the ultrasound apparatus 100 may extract a partial image of the ultrasound image that corresponds to the touch input. For example, the partial image may have a predetermined size, and the ultrasound apparatus 100 may extract the partial image based on the position of the touch screen at which the touch input is detected. The predetermined size may vary according to a system environment or user setting.

The ultrasound apparatus 100 may capture the partial image corresponding to the touch input and then may generate a copy image of the partial image.

The ultrasound apparatus 100 may extract a partial image corresponding to a touch input at regular intervals. The ultrasound apparatus 100 may extract a partial image when the position at which the touch input is detected is changed.

In operation S440, the ultrasound apparatus 100 may display the copy image of the partial image on a second area that is different from the first area on which the ultrasound image is displayed. That is, according to the present exemplary embodiment, the ultrasound apparatus 100 may display the copy image on an area on which the ultrasound image is not displayed.

The ultrasound apparatus 100 may display the copy image on the second area, which is also different from a third area on which a control panel with respect to a control of parameter values related to the ultrasound image is displayed as a GUI. That is, the ultrasound apparatus 100 may display the copy image on an area other than the first area that displays the ultrasound image and the third area that displays the control panel as the GUI.

The ultrasound apparatus 100 may display the copy image obtained by capturing the partial image having the predetermined size, on the second area. According to the present exemplary embodiment, the ultrasound apparatus 100 may display the copy image so that an object that is displayed at the position at which the touch input is detected may be located at a center of the second area. The object may include, but is not limited to, at least one of the reference point or the reference line with respect to selection of a measurement portion or a measurement area, the sample volume, and the body marker.

The ultrasound apparatus 100 may synchronize in real-time a partial image and a copy image that corresponds to the partial image, wherein the partial image is changed according to drag inputs, and may display the copy image on the second area. The user may watch the copy image displayed on the second area, thereby recognizing in real-time a portion of the ultrasound image which is obstructed by a touch instrument (e.g., a finger or an electronic pen).

The ultrasound apparatus 100 may display a copy image on the second area, wherein the copy image is obtained by magnifying or reducing the partial image by a predetermined ratio, and the partial image is extracted with respect to the position at which the touch input is detected. The predetermined ratio may vary according to a system environment or user setting.

According to the present exemplary embodiment, when the ultrasound apparatus 100 no longer detects the touch input, the ultrasound apparatus 100 may remove the copy image from the second area. That is, when the user no longer touches the touch screen with the finger or the electronic pen, the copy image may disappear from the touch screen.

Hereinafter, with reference to FIGS. 5A and 5B, the first area, the second area, and the third area that are displayed on the touch screen are described below.

Figure 5B:
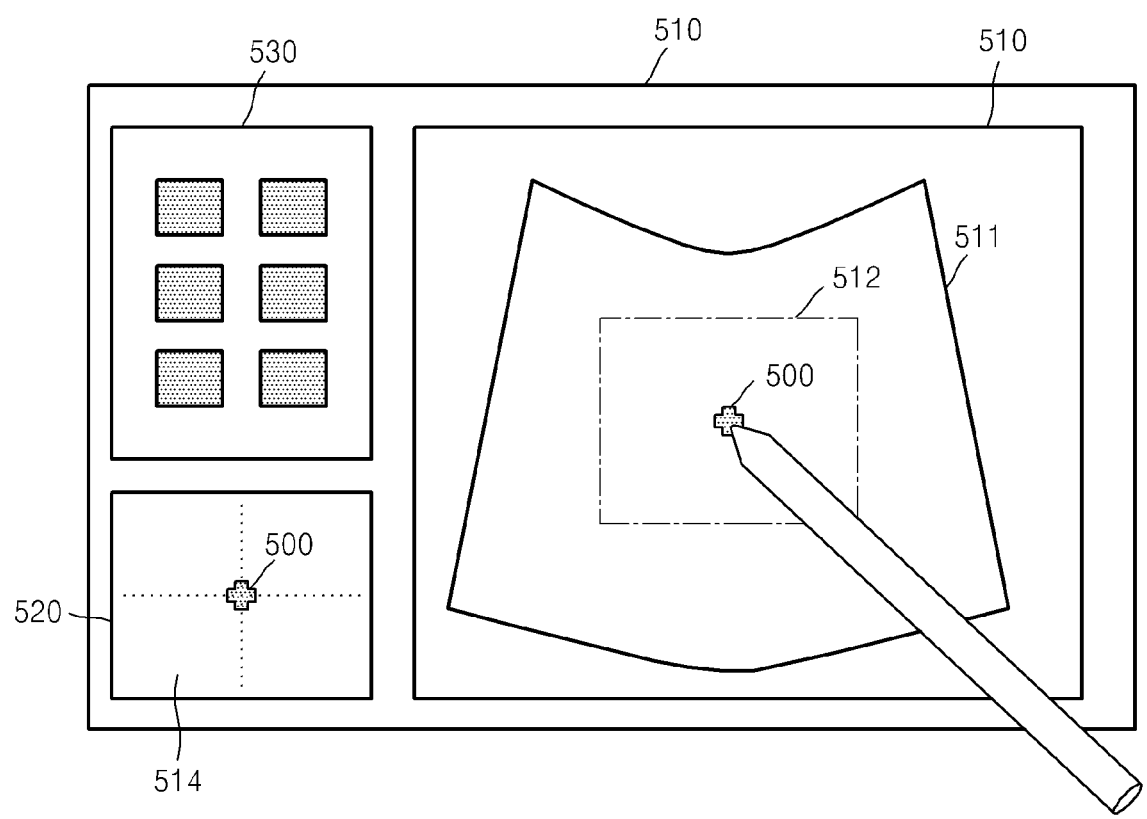

FIGS. 5A and 5B illustrate the display 110 of the ultrasound apparatus 100, according to an exemplary embodiment.

As illustrated in FIG. 5A, the display 110 of the ultrasound apparatus 100 may divide a touch screen into a first area 510, a second area 520, and a third area 530, but the division is not limited thereto.

The first area 510 may be a preset area of the touch screen on which an ultrasound image 511 is displayed. The second area 520 may be an area on which a copy image of a partial image corresponding to a touch input is displayed. The third area 530 may be an area on which a control panel while in a predetermined mode (e.g., a B mode, a Doppler mode, an M mode, or the like) is displayed as a GUI.

A position or a size of each of the first, second, and third areas 510, 520, and 530 may vary according to a system or user setting. In particular, the ultrasound apparatus 100 may select the second area 520 in areas that do not overlap with the first area 510 and the third area 530. That is, a position of the control panel and a position of an area that displays an ultrasound image may be changed according to modes; thus, the ultrasound apparatus 100 may adaptively select the second area 520 on which the copy image is displayed.

In the present exemplary embodiment, when a user touches a specific portion of the ultrasound image 511 by using a finger, the ultrasound apparatus 100 may detect a touch input by the user with respect to the ultrasound image 511 that is displayed on the first area 510. Here, since an object 500 that is displayed on the touched portion is obstructed by the finger, it is difficult for the user to recognize whether the user exactly touches a user-desired portion.

As illustrated in FIG. 5B, the user may touch a specific portion of the ultrasound image 511 by using an electronic pen (e.g., a stylus pen). Here, since an object 500 that is displayed on the touched portion is obstructed by the pen, it is difficult for the user to see whether a user-desired portion is in fact touched.

Thus, the ultrasound apparatus 100 may extract a partial image 512 corresponding to the touch input and may display a copy image 514 of the partial image 512, on the second area 520. For example, the ultrasound apparatus 100 may extract the partial image 512 having a size (e.g., 3 cm×3 cm) with respect to a position at which the touch input is detected. Then, the ultrasound apparatus 100 may display the copy image obtained by capturing the partial image 512, on the second area 520. The ultrasound apparatus 100 may display the copy image so that the object 500 that is displayed at the position at which the touch input is detected may be located at a center of the second area 520.

In this case, the user may exactly recognize at which point in the ultrasound image 511 the user-touched portion is positioned, by referring to the copy image. For example, when the user measures a size of a tumor or a girth of a fetus, the user may check the copy image, thereby selecting an exact measurement portion.

When the ultrasound apparatus 100 detects a drag input that starts at the position at which the touch input is detected, the ultrasound apparatus 100 may move the object 500, which is displayed at the position at which the touch input is detected, according to the drag input, and may display the copy image displayed on the second region 520 after changing the copy image in real-time.

In the present exemplary embodiment, the ultrasound apparatus 100 may display the copy image on the second area 520 adjacent to the first area 510 on which the ultrasound image 511 is displayed, so that a view of the user is not distracted.

Hereinafter, a method of providing a copy image during a predetermined mode, performed by the ultrasound apparatus 100, will be described in detail with reference to an exemplary embodiment of FIGS. 6A, 6B and 6C.

Figure 6A:
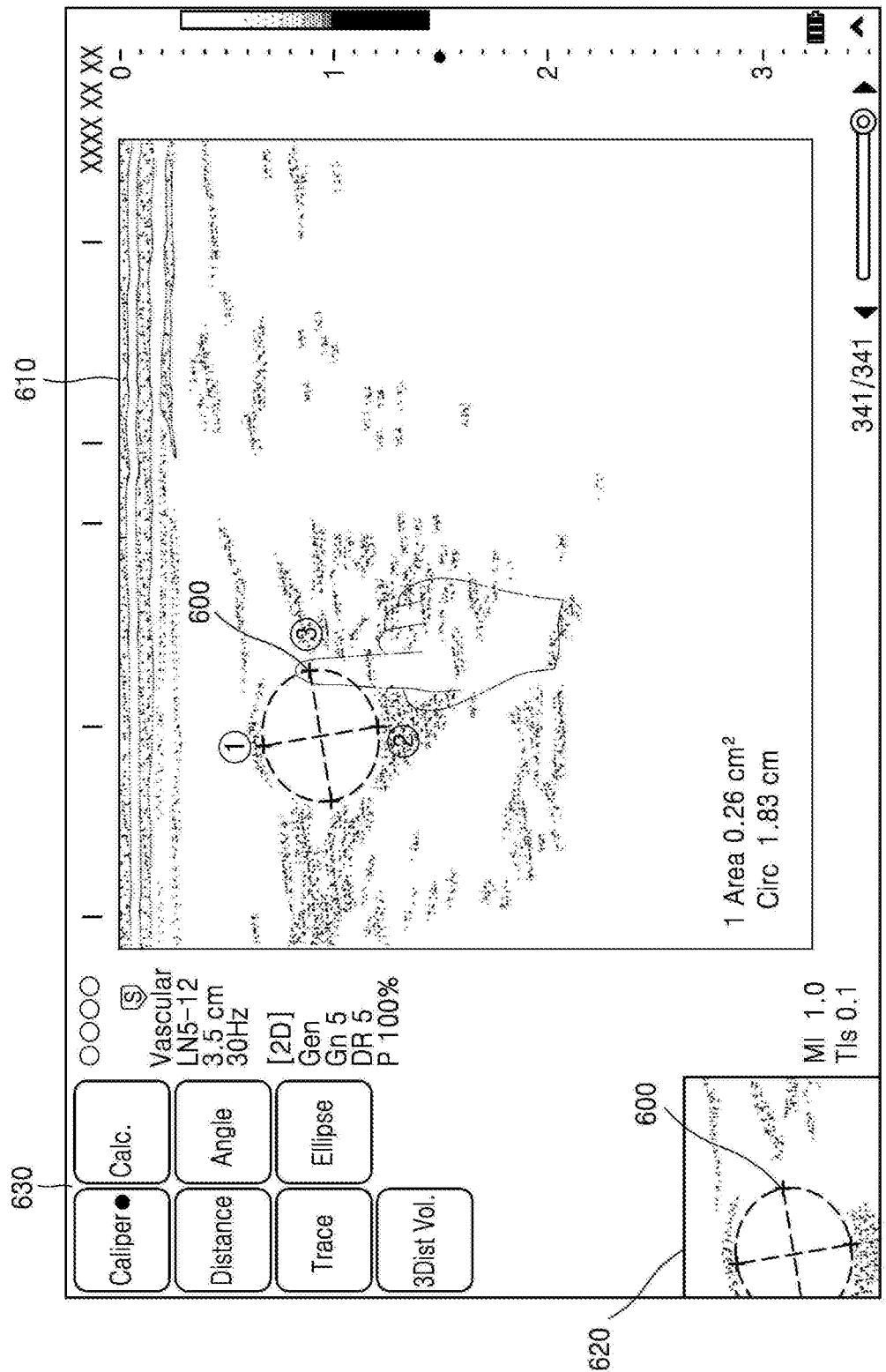
FIGS. 6A, 6B, and 6C illustrate screens for providing a copy image of a reference point at which the ultrasound apparatus selects a measurement area, according to an exemplary embodiment.
Figure 6B:
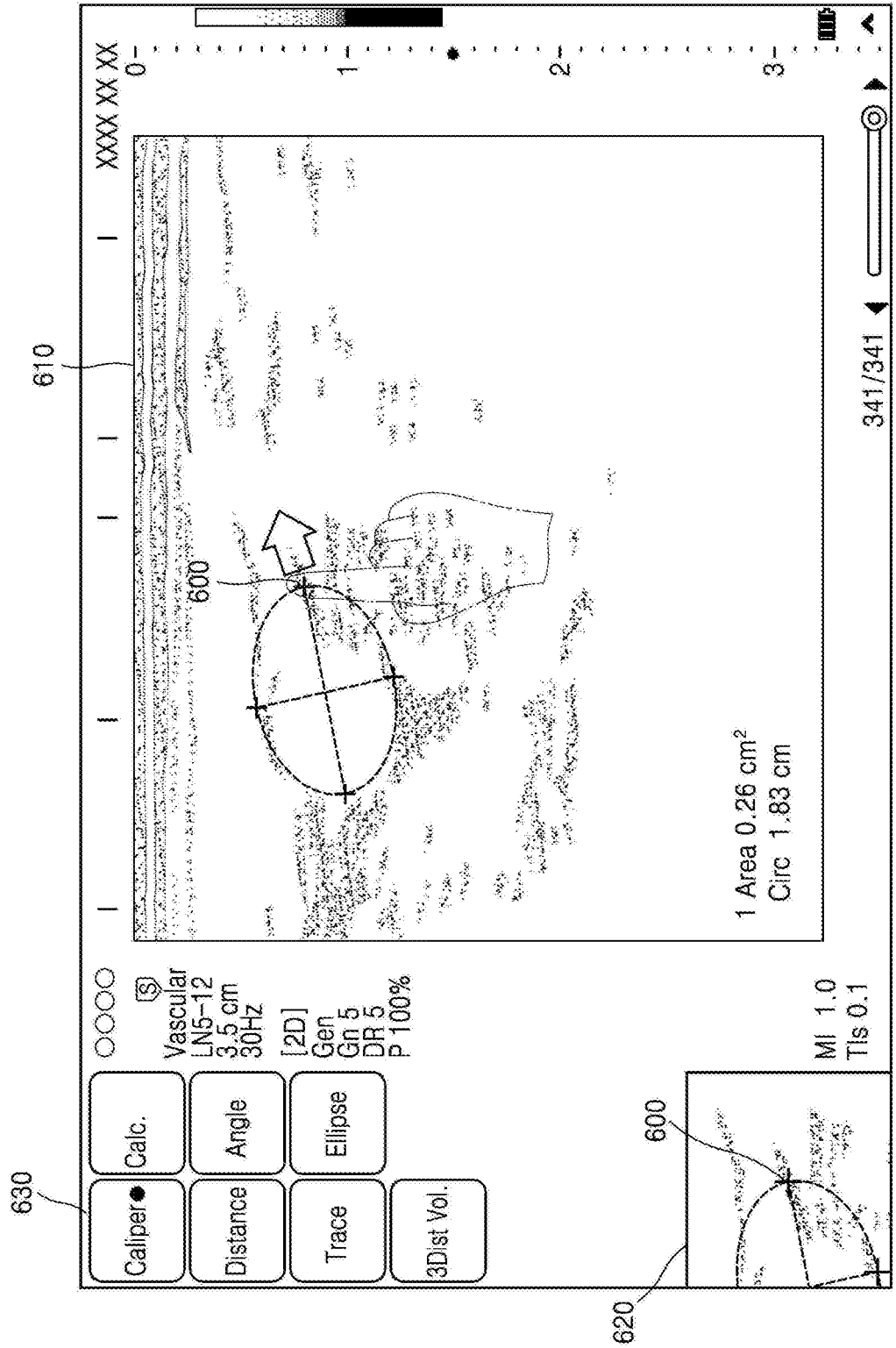
Figure 6C:
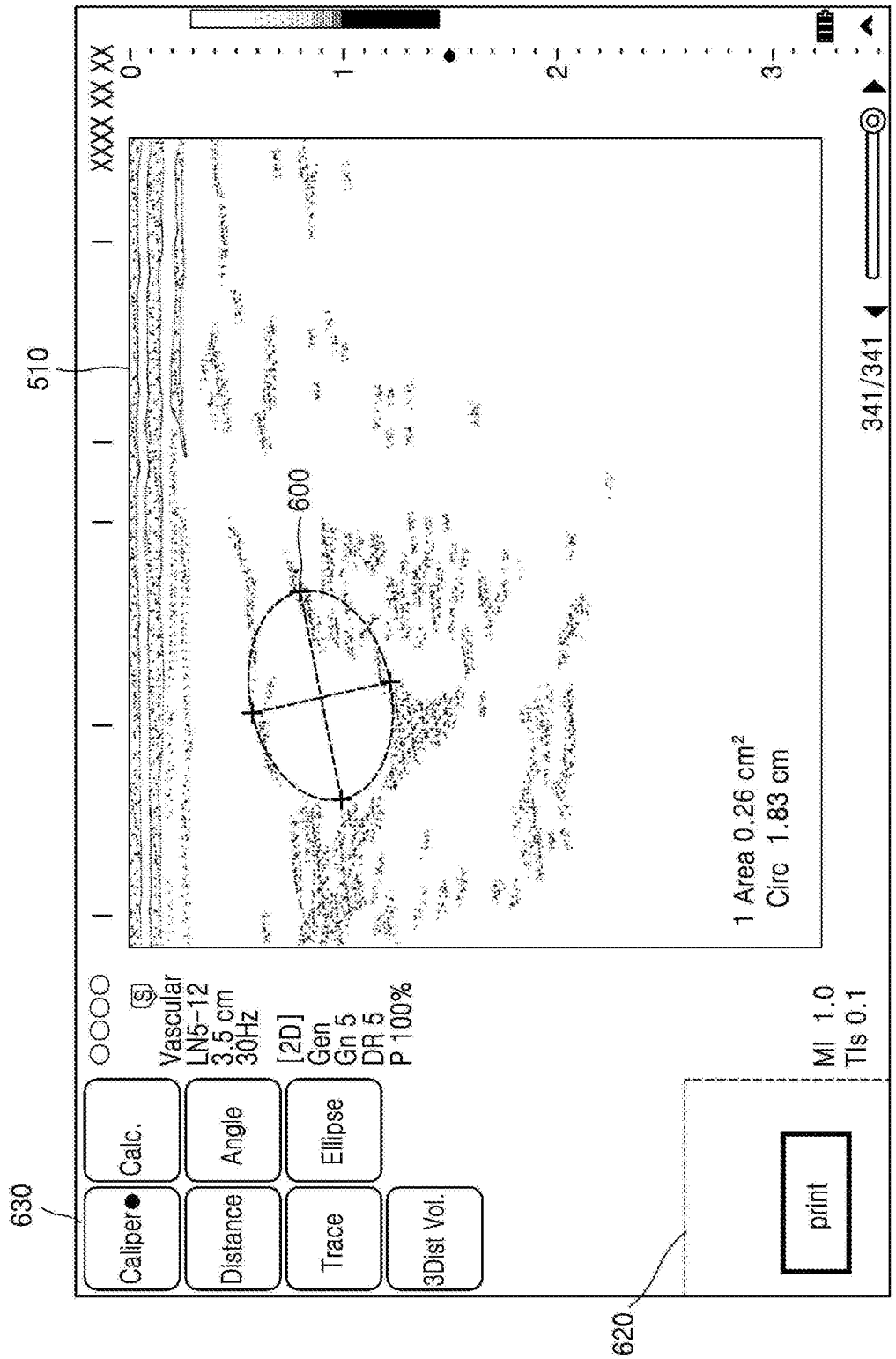

FIGS. 6A to 6C illustrate screens for providing a copy image of a reference point at which the ultrasound apparatus 100 selects a measurement area, according to an exemplary embodiment.

As illustrated in FIG. 6A, when a user selects a Caliper button and then selects an Ellipse button of a control panel that is displayed on a third area 630, touches and drags from a first portion① of an ultrasound image to a second portion② of the ultrasound image, and then takes off a finger, the ultrasound apparatus 100 may display an oval-shape object for selection of a measurement area on a first area 610. The user may leftward or rightward drag a cross-shape reference point 600 that is displayed on a third portion③; thus, the user may adjust a size of the measurement area.

When the user touches the third portion③, the ultrasound apparatus 100 may display a copy image having a predetermined size with respect to a user-touched portion, on a second area 620. The cross-shape reference point 600 that is displayed on the third portion③ may be located at a center of the second area 620.

As illustrated in FIG. 6B, when the user touches and simultaneously rightward drags the cross-shape reference point 600 that is displayed on the third portion③, a point at which a touch input is detected is continuously changed according to drag inputs, so that the ultrasound apparatus 100 may change a copy image in real-time with respect to the point at which the touch input is detected and may display the copy image on the second area 620. That is, the copy image having a predetermined size with respect to the cross-shape reference point 600 may be changed in real-time and may be displayed on the second area 620.

The user may recognize an exact position of the cross-shape reference point 600, which is obstructed by a finger, in the first area 610 by referring to the copy image displayed on the second area 620. That is, the ultrasound apparatus 100 may help the user to exactly measure a size of a tumor or the like, which is very important in a disease diagnosis or the like.

As illustrated in FIG. 6C, when the user takes off the finger from the touch screen, the ultrasound apparatus 100 no longer displays the copy image on the second area 620.

In the present exemplary embodiment, the ultrasound apparatus 100 may help the user to exactly recognize a reference point, which is obstructed by a touch instrument (e.g., a finger or an electronic pen), by using the copy image.

Hereinafter, a method of displaying an object on a screen, the method performed by the ultrasound apparatus 100 to allow a user to touch, to drag and to freely move the object that is activated with respect to its motion, will now be described in detail with reference to FIGS. 7 through 9.

Figure 7:
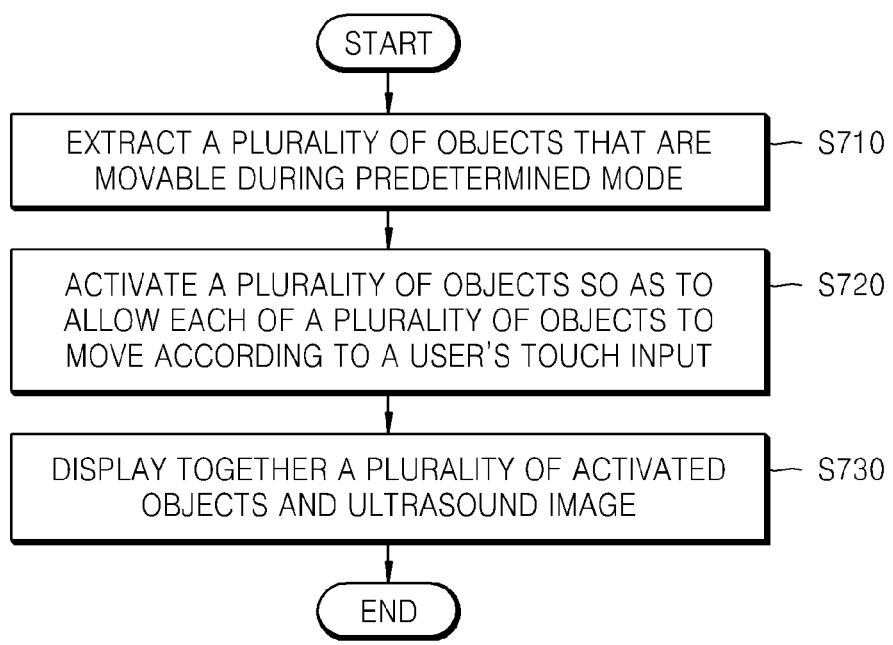
FIG. 7 is a flowchart of a method of displaying an object, according to an exemplary embodiment.

FIG. 7 is a flowchart of a method of displaying an object, the method performed by the ultrasound apparatus 100, according to an exemplary embodiment.

In operation S710, the ultrasound apparatus 100 may extract a plurality of objects that are movable during a predetermined mode.

The predetermined mode may include a measurement mode, an annotation input mode, a Doppler mode, an M mode, or the like. During the measurement mode, a circumference, a length, a size, or the like of an interest area may be measured, a maximum speed, an instantaneous speed, a slope, or the like in a predetermined sample volume may be measured, or speed variation according to time may be measured. Functions of the annotation input mode, the Doppler mode, and the M mode are known to one of ordinary skill in the art, thus, detailed descriptions thereof are omitted here.

The plurality of objects that are movable during the predetermined mode indicate objects that are movable according to a user's touch input, when the objects are activated. For example, each of the objects may include, but is not limited to, at least one of a reference point, a reference line, annotation, and an arrow which are used in selecting a measurement point or a measurement area.

The objects may be a same type of objects or different types of objects. The objects may include a first reference point and a second reference point. The objects may include a first reference point and a sample volume, or a first reference point and annotation.

In operation S720, the ultrasound apparatus 100 may activate the objects to allow each of the extracted objects to move according to a user's touch input. That is, in order to allow a user to freely move each of the extracted objects by performing a touch input, the ultrasound apparatus 100 may activate all of the objects.

In operation S730, the ultrasound apparatus 100 may display together the activated objects and an ultrasound image. In the present exemplary embodiment, the ultrasound image may include, but is not limited to, a B mode image, a Doppler image, an M mode image, and an elasticity mode image.

The ultrasound apparatus 100 may display the activated objects on the ultrasound image. In an exemplary embodiment, the ultrasound apparatus 100 may display the activated objects to partially overlap with the ultrasound image, or may display the activated objects in an area of a screen which is different from another area of the screen on which the ultrasound image is displayed.

In the present exemplary embodiment, the ultrasound apparatus 100 may receive a touch and drag input with respect to at least one object from among the activated objects. In this case, the ultrasound apparatus 100 may move the at least one object according to the touch and drag input and may display the at least one object.

When sizes of objects related to the ultrasound image are small, it is difficult for the user to exactly select an object by performing a touch input. Also, although the user exactly touches the object by using a touch instrument, the object is obstructed by the touch instrument, such that it is difficult for the user to recognize an exact position of the object. Thus, in the present exemplary embodiment, the ultrasound apparatus 100 may expand a touch recognition range in which the object is recognized as being selected.

For example, the ultrasound apparatus 100 receives a touch and drag input with respect to a first area within a predetermined radius from a point at which an activated first object is displayed, the ultrasound apparatus 100 may recognize that the ultrasound apparatus 100 has received the touch and drag input with respect to the first object. Also, when the ultrasound apparatus 100 receives a touch and drag input with respect to a second area within the predetermined radius from a point at which a second object from among the activated objects is displayed, the ultrasound apparatus 100 may move the second object according to the touch and drag input with respect to the second area and may display the second object.

According to exemplary embodiments, a touch recognition range of the first object and a touch recognition range of the second object may overlap with each other. When the user touches and drags the overlapped area, the ultrasound apparatus 100 may move one of the first and second objects and then may display the moved object, according to priority order information. The priority order information means information with respect to which object from among a plurality of objects is determined to be selected when the user performs a touch input on an area in which touch recognition ranges of the plurality of objects overlap with each other.

For example, in a case where movement priority orders of the plurality of objects are preset, the ultrasound apparatus 100 may move one of the first and second objects according to the preset movement priority orders. For example, if the priority order is set so that a lastly-moved object has a lower priority, the ultrasound apparatus 100 may compare movement time information of the first object with movement time information of the second object, and may move one of the first and second objects, which has an earlier movement time, according to the comparison result. Exemplary embodiments in which a touch recognition range with respect to an object expands will be described in detail with reference to FIGS. 17 through 19.

Figure 8A:
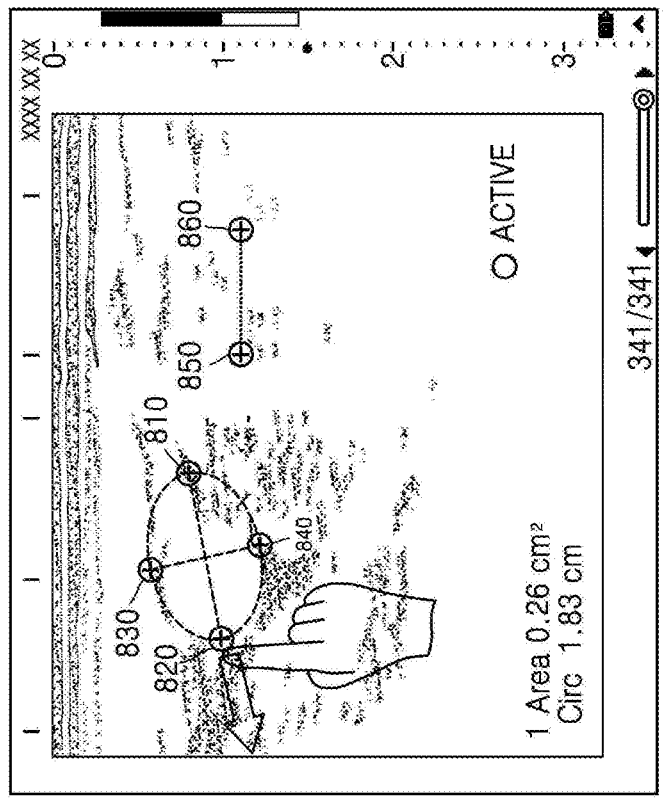
FIGS. 8A and 8B illustrate a plurality of activated objects, according to an exemplary embodiment.
Figure 8B:
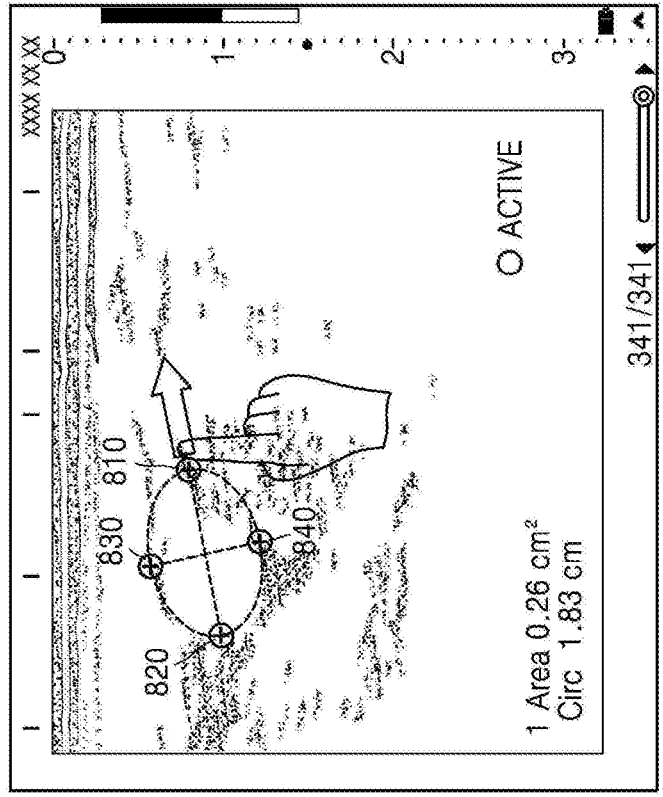

FIGS. 8A and 8B illustrate a plurality of activated objects, according to an exemplary embodiment.

As illustrated in FIG. 8A, when a measurement mode for measuring a size or a circumference of an interest area is selected, the ultrasound apparatus 100 may extract movable objects during the measurement mode.

For example, in a case where a user selects a caliper button and an Ellipse button of a control panel, touches and simultaneously drags a third reference point 830 of an ultrasound image to a fourth reference point 840, and then takes off a finger, the ultrasound apparatus 100 may display an oval enabled for selecting a measurement area on the ultrasound image. The ultrasound apparatus 100 may extract a first reference point 810, a second reference point 820, the third reference point 830, and the fourth reference point 840 as the movable objects during the measurement mode.

Afterward, the ultrasound apparatus 100 may activate all of the first reference point 810, the second reference point 820, the third reference point 830, and the fourth reference point 840. Thus, the user may move a position of the first reference point 810 by instantly touching and dragging the first reference point 810 in a right direction, without separate manipulation.

As illustrated in FIG. 8B, the user may move a position of the second reference point 820 by directly touching and dragging the second reference point 820 without separately inactivating the first reference point 810 and activating the second reference point 820.

When a length measurement line is added according to a user input, the ultrasound apparatus 100 may extract objects (e.g., a fifth reference point 850 and a six reference point 860) that are movable on the length measurement line, and may activate all of the extracted objects (e.g., the fifth reference point 850 and the sixth reference point 860).

Thus, the user may freely move a measurement reference point by touching the activated objects (i.e., the first through sixth objects 810 through 860). That is, according to the present exemplary embodiment, the ultrasound apparatus 100 may improve convenience of the user who uses a touch interface, and may allow rapid measurement and diagnosis.

Figure 9:
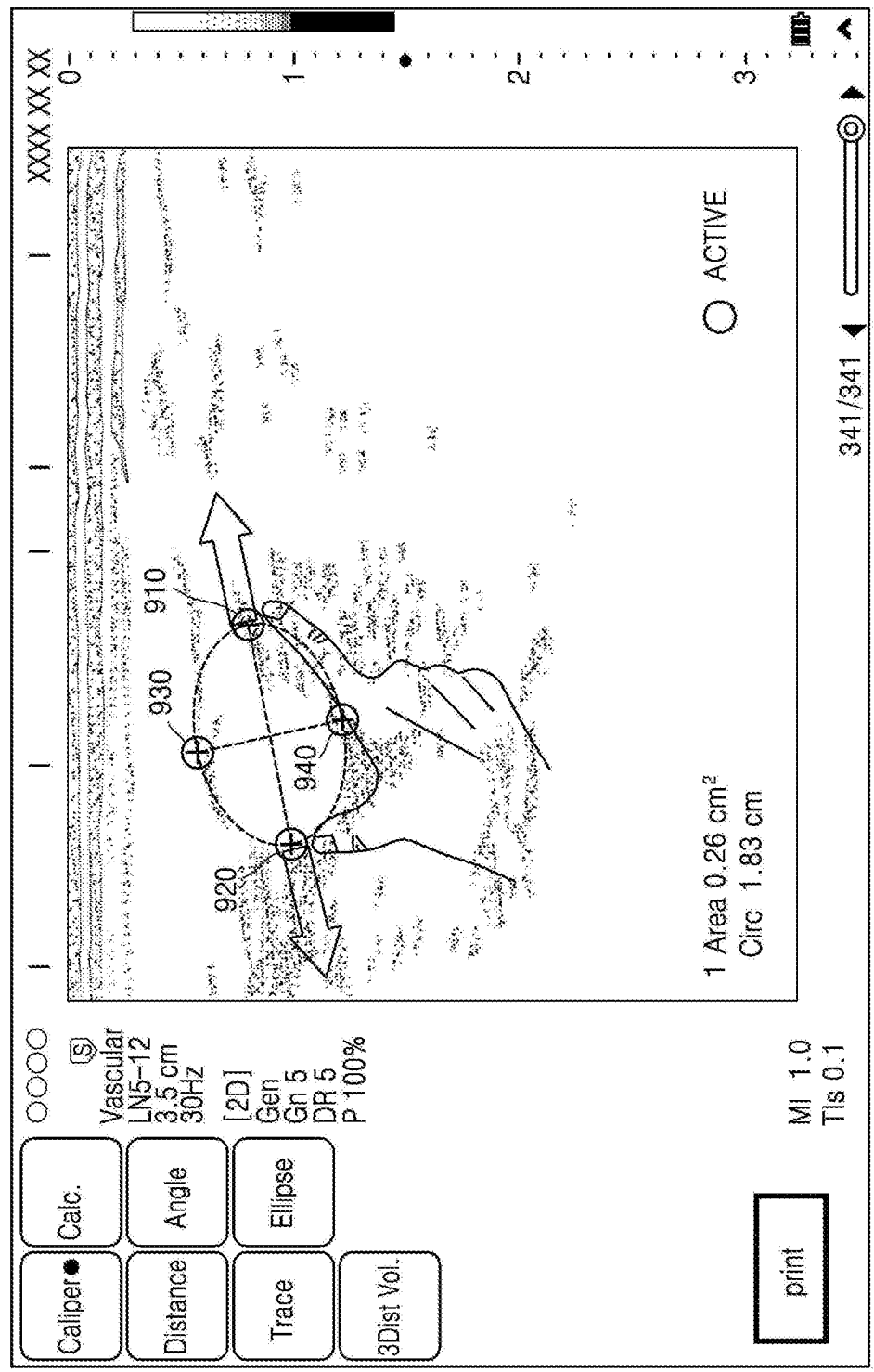
FIG. 9 illustrates an example in which a plurality of activated objects are moved according to multiple touch inputs.

FIG. 9 illustrates an example in which a plurality of activated objects are moved according to multiple touch inputs.

As illustrated in FIG. 9, the ultrasound apparatus 100 may receive the multiple touch inputs with respect to a first object and a second object included in the activated objects. The ultrasound apparatus 100 may move each of the first and second objects according to the multiple touch inputs and may display them.

For example, in a case where a user selects a caliper button and an Ellipse button of a control panel, touches and simultaneously drags a third reference point 930 of an ultrasound image to a fourth reference point 940, and then takes off a finger, the ultrasound apparatus 100 may display an oval enabled for selecting a measurement area on the ultrasound image. The ultrasound apparatus 100 may extract a first reference point 910, a second reference point 920, the third reference point 930, and the fourth reference point 940 as movable objects during a measurement mode.

Thus, the user may move two fingers in different directions while the user touches the first reference point 910 and the second reference point 920, with the two fingers. The ultrasound apparatus 100 may move each of the first reference point 910 and the second reference point 920, and thus therefore adjust a length of a long axis of the oval enabled for selecting the measurement area.

Figure 10A:
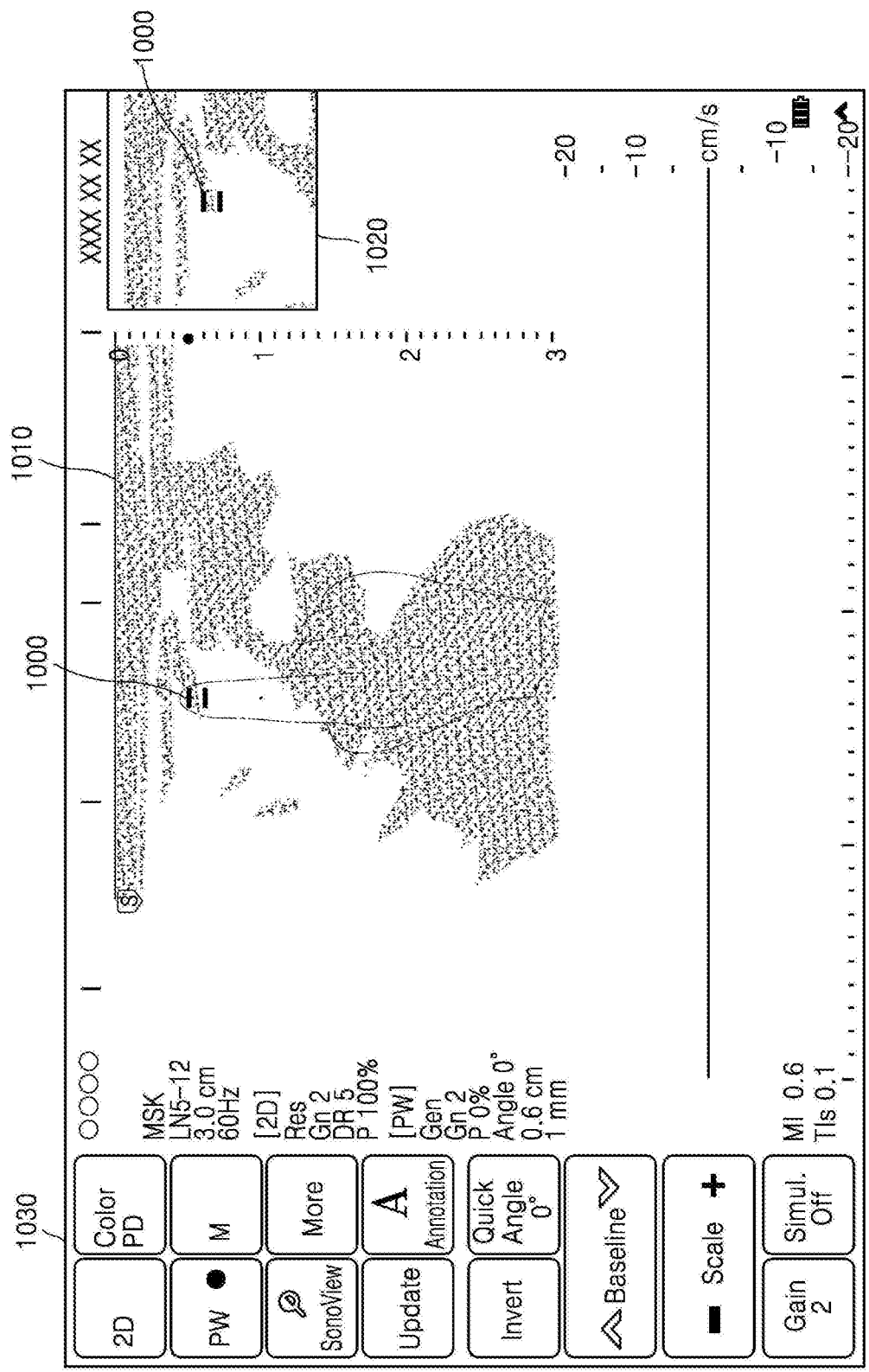
FIGS. 10A and 10B illustrate screens for providing a copy image related to a sample volume, according to an exemplary embodiment.
Figure 10B:
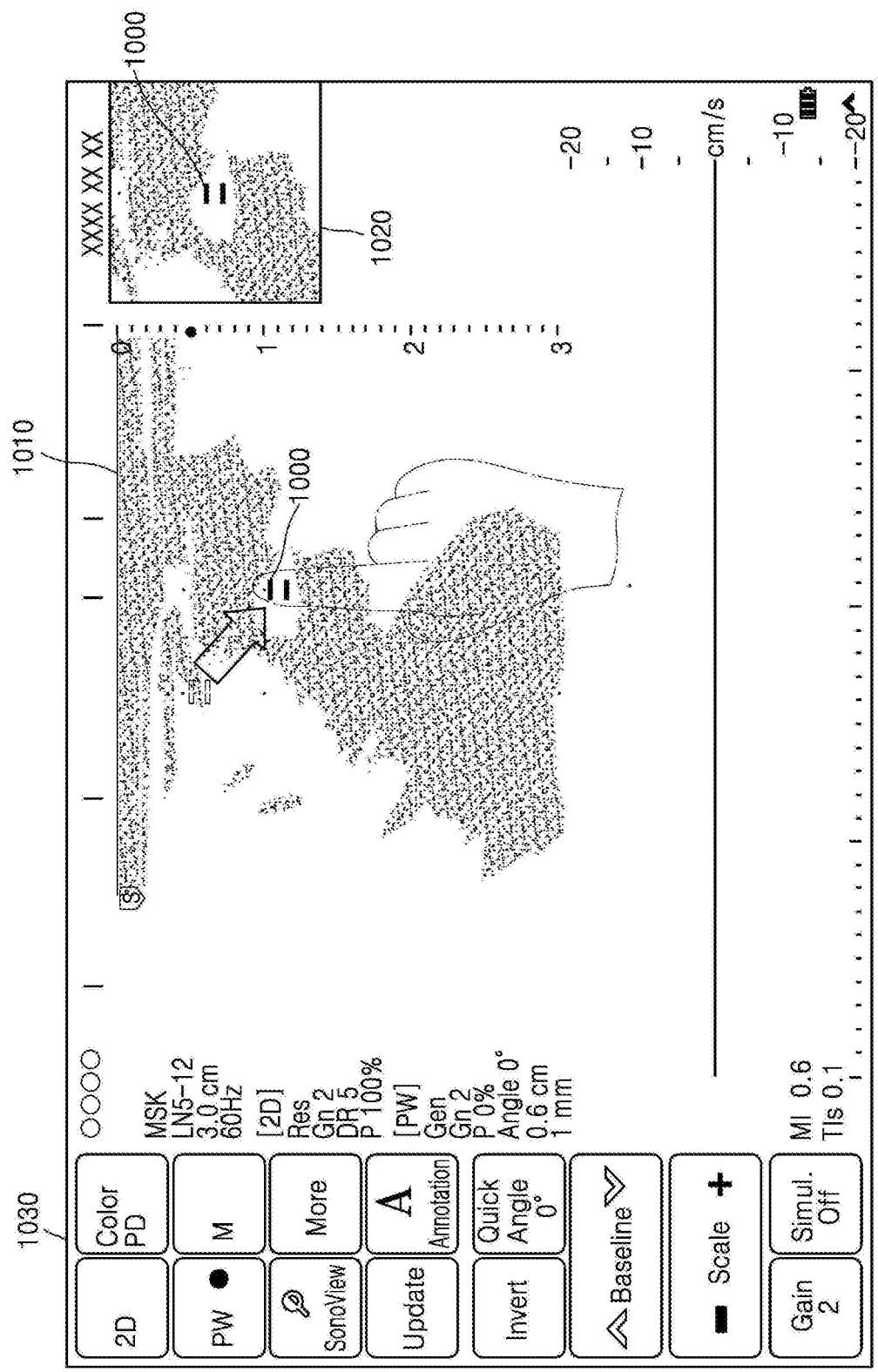

FIGS. 10A and 10B illustrate screens for providing a copy image related to a sample volume 600, performed by the ultrasound apparatus 100, according to an exemplary embodiment.

As illustrated in FIG. 10A, when a user selects a PW button of a control panel displayed on a third area 1030, the ultrasound apparatus 100 may detect user selection and then may display a sample volume 1000 on a B mode image. In this case, the user may touch and simultaneously move the sample volume 1000, thereby selecting a measurement position (e.g., a predetermined blood vessel) for observation of a Doppler image.

When the user touches the sample volume 1000, the sample volume 1000 and an ultrasound image around the sample volume 1000 are obstructed by a finger. Thus, the ultrasound apparatus 100 may display a copy image having a predetermined size with respect to a user-touched portion, on a second area 1020. The sample volume 1000 that is displayed on the user-touched portion may be located at a center of the second area 1020.

As illustrated in FIG. 10B, when the user touches and simultaneously drags the sample volume 1000, a point at which a touch input is detected is continuously changed according to drag inputs, so that the ultrasound apparatus 100 may change a copy image in real-time with respect to the point at which the touch input is detected and may display the copy image on the second area 1020. That is, the copy image having a predetermined size with respect to the sample volume 1000 may be changed in real-time and may be displayed on the second area 1020.

The user may recognize an exact position of the sample volume 1000, which is obstructed by a finger, in the first area 1010 by referring to the copy image displayed on the second area 1020.

When the user moves the sample volume 1000 to a user-desired position and then takes off the finger from the touch screen, the ultrasound apparatus 100 no longer displays the copy image on the second area 1020. Then, the ultrasound apparatus 100 may provide the Doppler image about a blood vessel at which the sample volume 1000 is positioned.

In the present exemplary embodiment, the ultrasound apparatus 100 may allow the user to recognize a position of the sample volume 1000, which is obstructed by a touch instrument (e.g., a finger or an electronic pen), by using the copy image, so that the ultrasound apparatus 100 may help the user to exactly select a target blood vessel for a Doppler image.

Figure 11A:
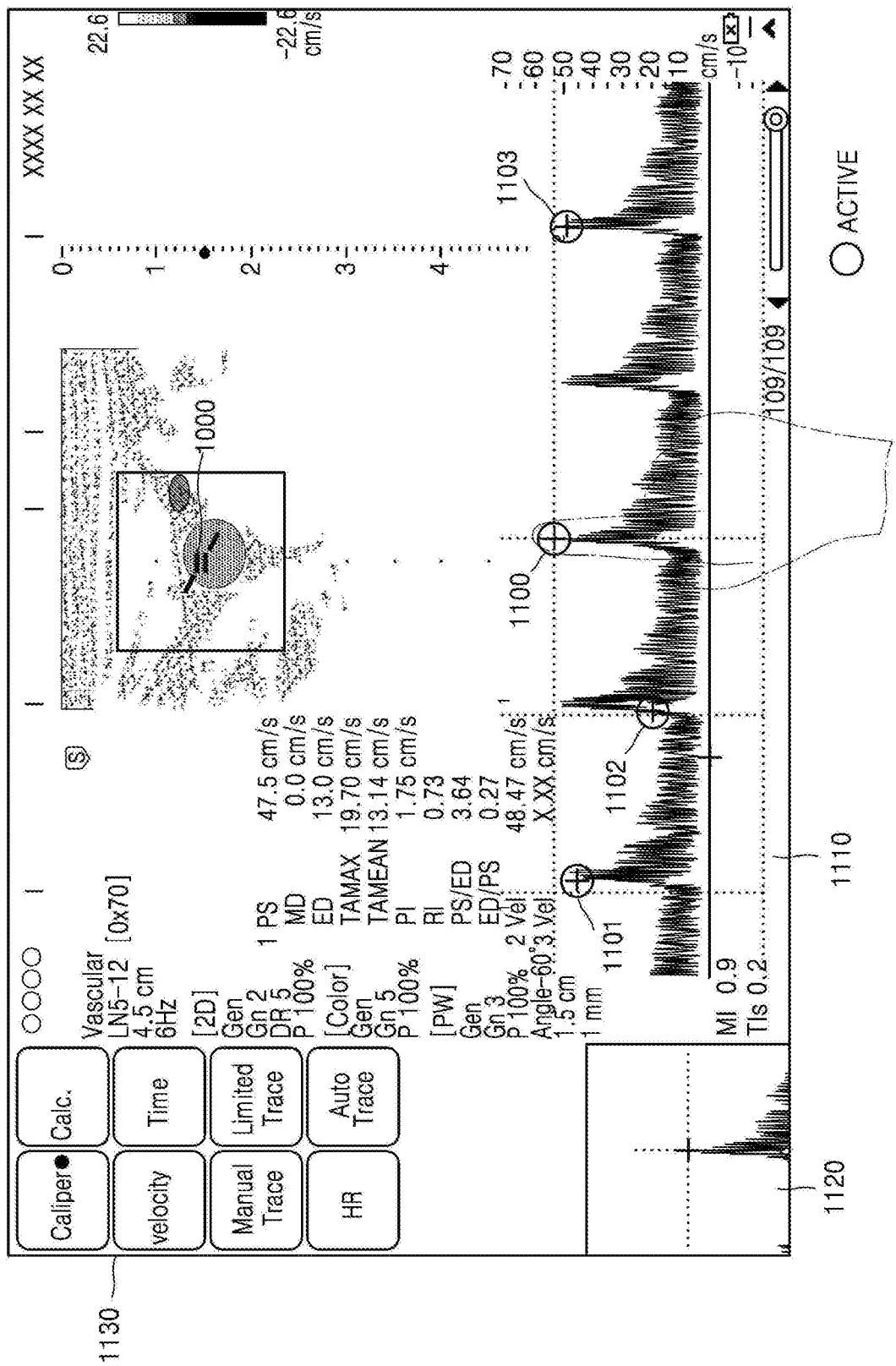
FIGS. 11A and 11B illustrate screens for providing a copy image and a plurality of activated objects related to a Doppler image, according to an exemplary embodiment.
Figure 11B:
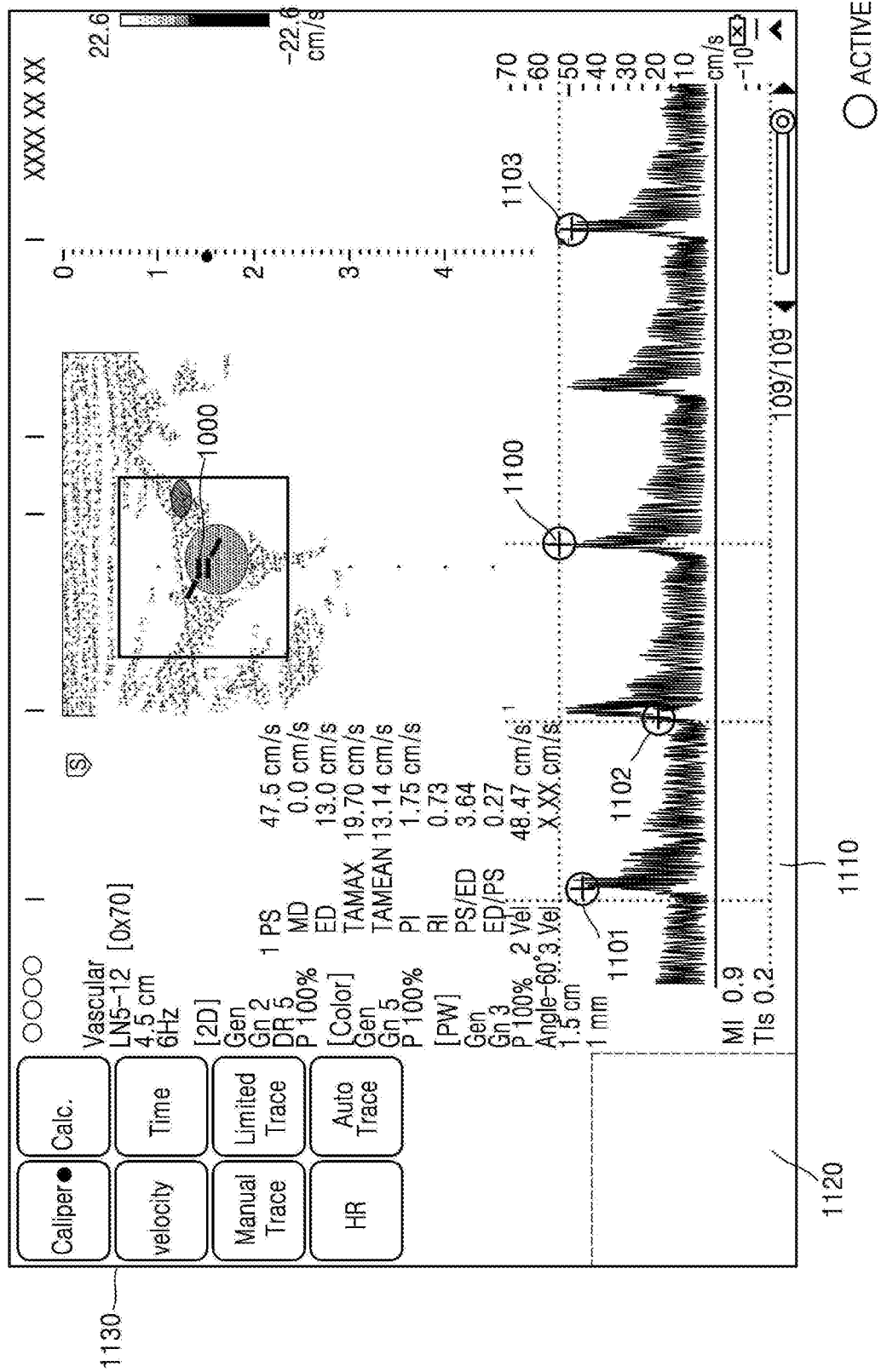

FIGS. 11A and 11B illustrate screens for providing a copy image and a plurality of activated objects related to a Doppler image, performed by the ultrasound apparatus 100, according to an exemplary embodiment.

As illustrated in FIG. 11A, after a user adjusts a position of a sample volume, when the user selects a Caliper button and then selects a Velocity button of a control panel that is displayed on a third area 1130, the ultrasound apparatus 100 may display a reference line and reference points for measurement of a velocity of blood flow with respect to a Doppler image that is displayed on a first area 1110. The ultrasound apparatus 100 may activate all of a reference line and reference points 1100, 1101, 1102, and 1103 that are displayed on the screen, so that the reference line and the reference points 1100, 1101, 1102, and 1103 may be moved according to a user's touch input.

Thus, according to the present exemplary embodiment, the user may touch and simultaneously move the reference point 1100, thereby selecting a measurement position to measure a maximum velocity (cm/s) of a blood flow.

When the user touches the reference point 1100, the reference point 1100 and a Doppler image around the reference point 1100 are obstructed by a finger. Thus, the ultrasound apparatus 100 may display a copy image having a predetermined size with respect to a user-touched portion, on a second area 1120. The reference point 1100 that is displayed on the user-touched portion may be located at a center of the second area 1120.

When the user touches and simultaneously drags the reference point 1100, a point at which a touch input is detected is continuously changed according to drag inputs, so that the ultrasound apparatus 100 may change a copy image in real-time with respect to the point at which the touch input is detected and may display the copy image on the second area 1120. That is, the copy image having a predetermined size with respect to the reference point 1100 may be changed in real-time and may be displayed on the second area 1120.

The user may recognize the reference point 1100 and an image around the reference point 1100, which are obstructed by a finger, in the first area 1110 by referring to the copy image displayed on the second area 1120.

As illustrated in FIG. 11B, when the user moves the reference point 1100 to a user-desired position and then takes off the finger from the touch screen, the ultrasound apparatus 100 no longer displays the copy image on the second area 1120. Then, the ultrasound apparatus 100 may provide the maximum velocity (cm/s) at the reference point 1100.

Because the reference line and the reference points 1100, 1101, 1102, and 1103 that are displayed on the screen are all activated, the user may freely change positions of at least one of the reference points 1100, 1101, 1102, and 1103 by touching and dragging at least one of the reference points 1100, 1101, 1102, and 1103.

In the present exemplary embodiment, the ultrasound apparatus 100 may allow the user to exactly recognize a position of the reference point, which is obstructed by a touch instrument (e.g., a finger or an electronic pen), by using the copy image, so that the ultrasound apparatus 100 may help the user to exactly select a velocity measurement position in the Doppler image.

Figure 12A:
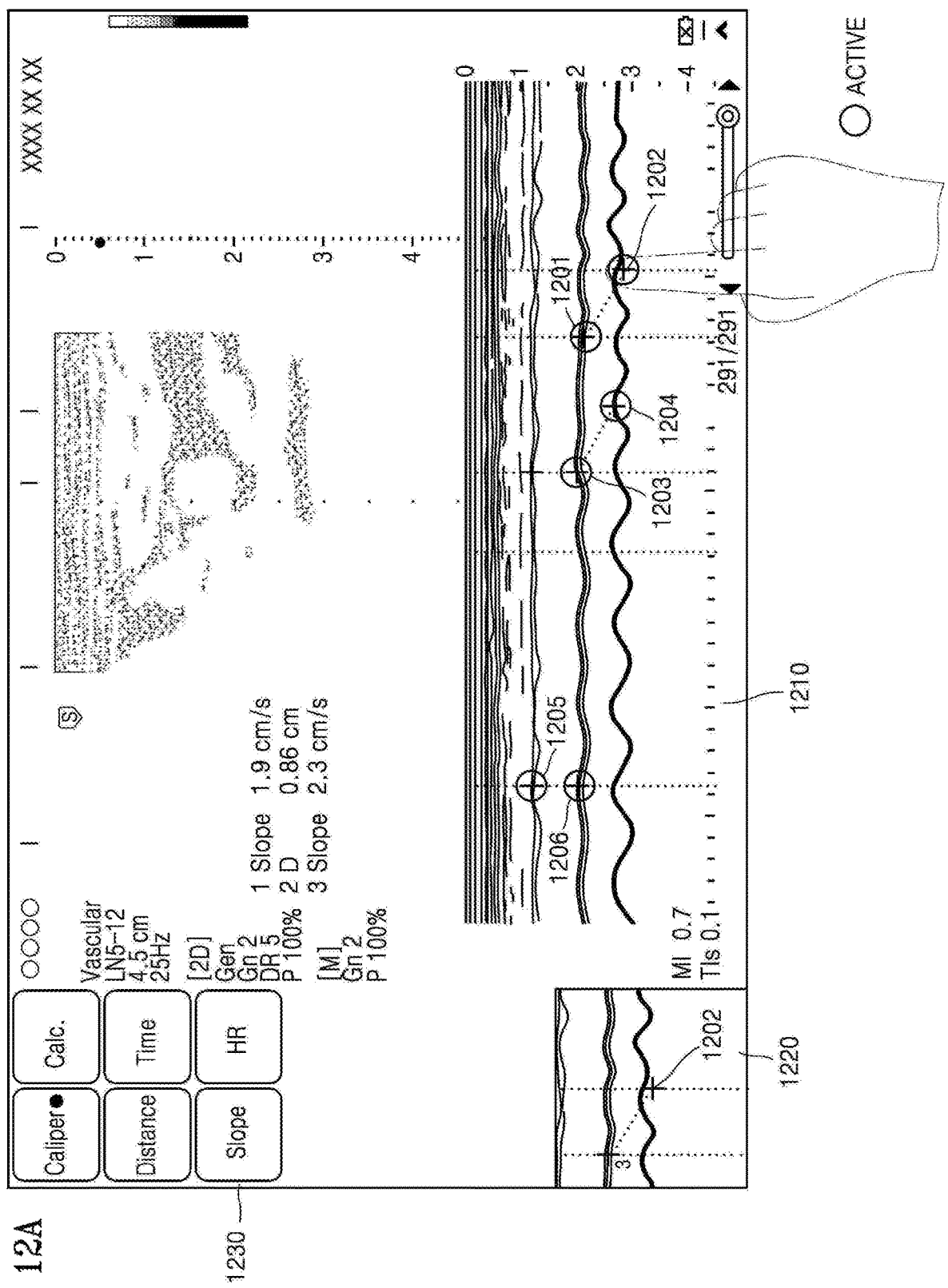
FIGS. 12A and 12B illustrate screens for providing a copy image and a plurality of activated objects related to an M mode image, according to an exemplary embodiment.
Figure 12B:
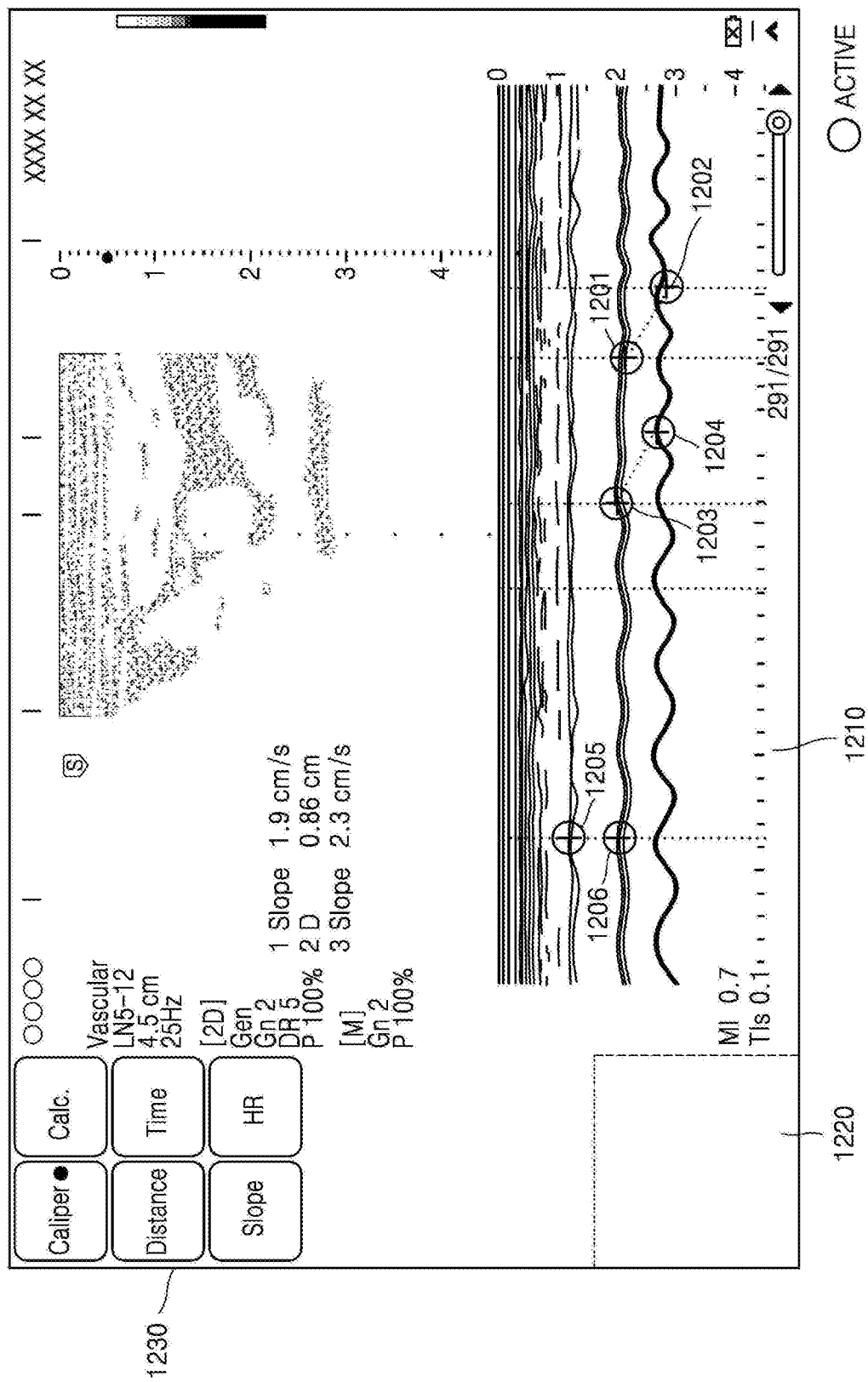

FIGS. 12A and 12B illustrate screens for providing a copy image and a plurality of activated objects related to an M mode image, performed by the ultrasound apparatus 100, according to an exemplary embodiment.

The M mode image indicates an image in which a motion of an organ is expressed as brightness, by using ultrasound echo signals that are repeatedly obtained with respect to one fixed scan line. The M mode image is mainly used in observing the motion of an organ such as the heart, which has valves that move fast. When there is no motion of the organ, the M mode image shows flat lines that are horizontally parallel to each other, but the flat lines may become waves according to the motion of the organ.

As illustrated in FIG. 12A, after a user adjusts a position of a reference line in the M mode image, when the user selects a Caliper button and then selects a Slope button of a control panel that is displayed on a third area 1230, the ultrasound apparatus 100 may display an object for measurement of a slope on the M mode image that is displayed on a first area 1210.

The user may touch and simultaneously make a dragging motion from a first portion corresponding to a first reference point 1201 of the M mode image to a second portion corresponding to a second reference point 1202 of the M mode image, thereby selecting a measurement position for the measurement of the slope. The ultrasound apparatus 100 may activate all of the objects corresponding to a first reference point 1201 displayed at the first portion and a second reference point 1202 displayed at the second portion. Thus, the user may minutely adjust the measurement position for the measurement of the slope by freely changing positions of the first object 1201 and the second object 1202 in a touch and drag manner. According to the present exemplary embodiment, objects corresponding to a third reference point 1203, a fourth reference point 1204, a fifth reference point 1205, and a sixth reference point 1206 that are movable on the M mode image may be all activated.

When the user performs dragging from the first reference point 1201 to the second reference point 1202 by using a finger, a position at which a touch input is detected is continuously changed, so that the ultrasound apparatus 100 may change a copy image in real-time with respect to the position at which the touch input is detected and may display the copy image on a second area 1220. For example, the user may recognize an exact position of a second reference point 1202, which is obstructed by a finger, in the first area 1210 by referring to the copy image displayed on the second area 1220.

As illustrated in FIG. 12B, when the user moves the reference point 1200 to a user-desired position and then takes off the finger from the touch screen, the ultrasound apparatus 100 no longer displays the copy image on the second area 1220.

Because reference points 1201, 1202, 1203, 1204, 1205, and 1206 that are displayed on the screen are all activated, the user may freely change positions of at least one of the reference points 1201, 1202, 1203, 1204, 1205, and 1206 by touching and dragging at least one of the reference points 1201, 1202, 1203, 1204, 1205, and 1206.

In the present exemplary embodiment, the ultrasound apparatus 100 may allow the user to exactly recognize a position of the reference point, which is obstructed by a touch instrument (e.g., a finger or an electronic pen), by using the copy image, so that the ultrasound apparatus 100 may help the user to exactly select a slope measurement position in the M mode image.

Figure 13A:
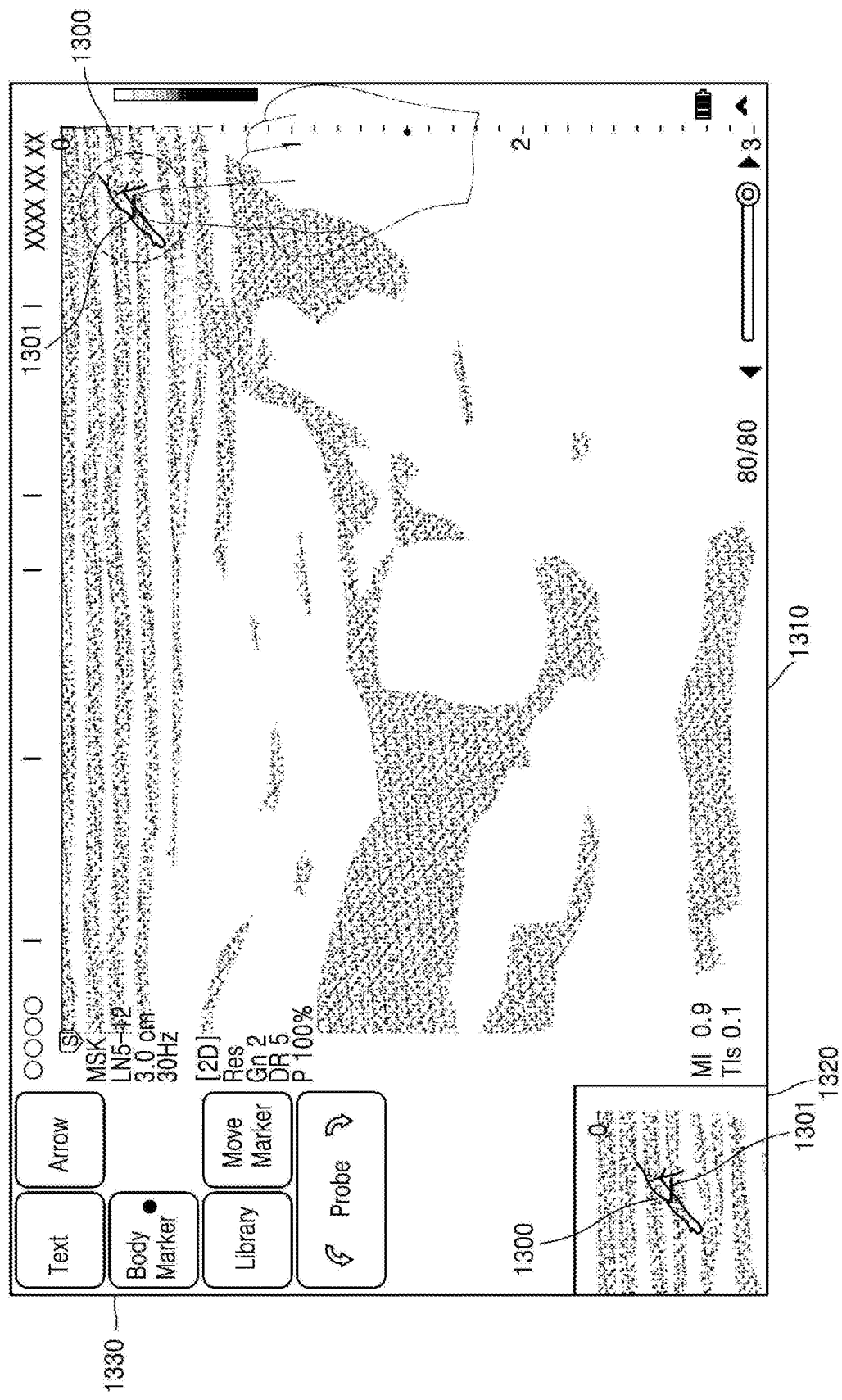
FIGS. 13A, 13B and 13C illustrate screens for providing a copy image related to generation of a body marker, according to an exemplary embodiment.
Figure 13B:
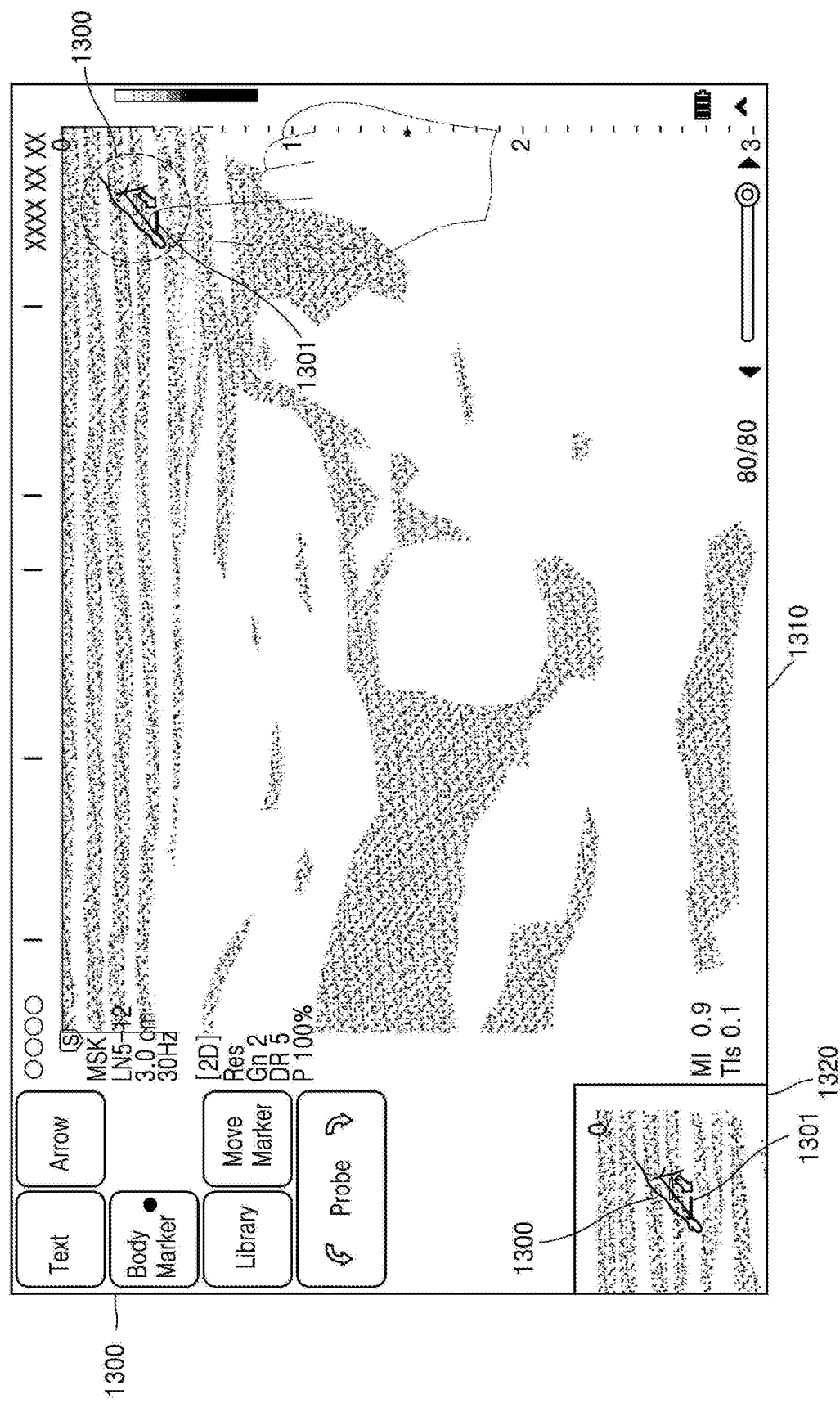
Figure 13C:
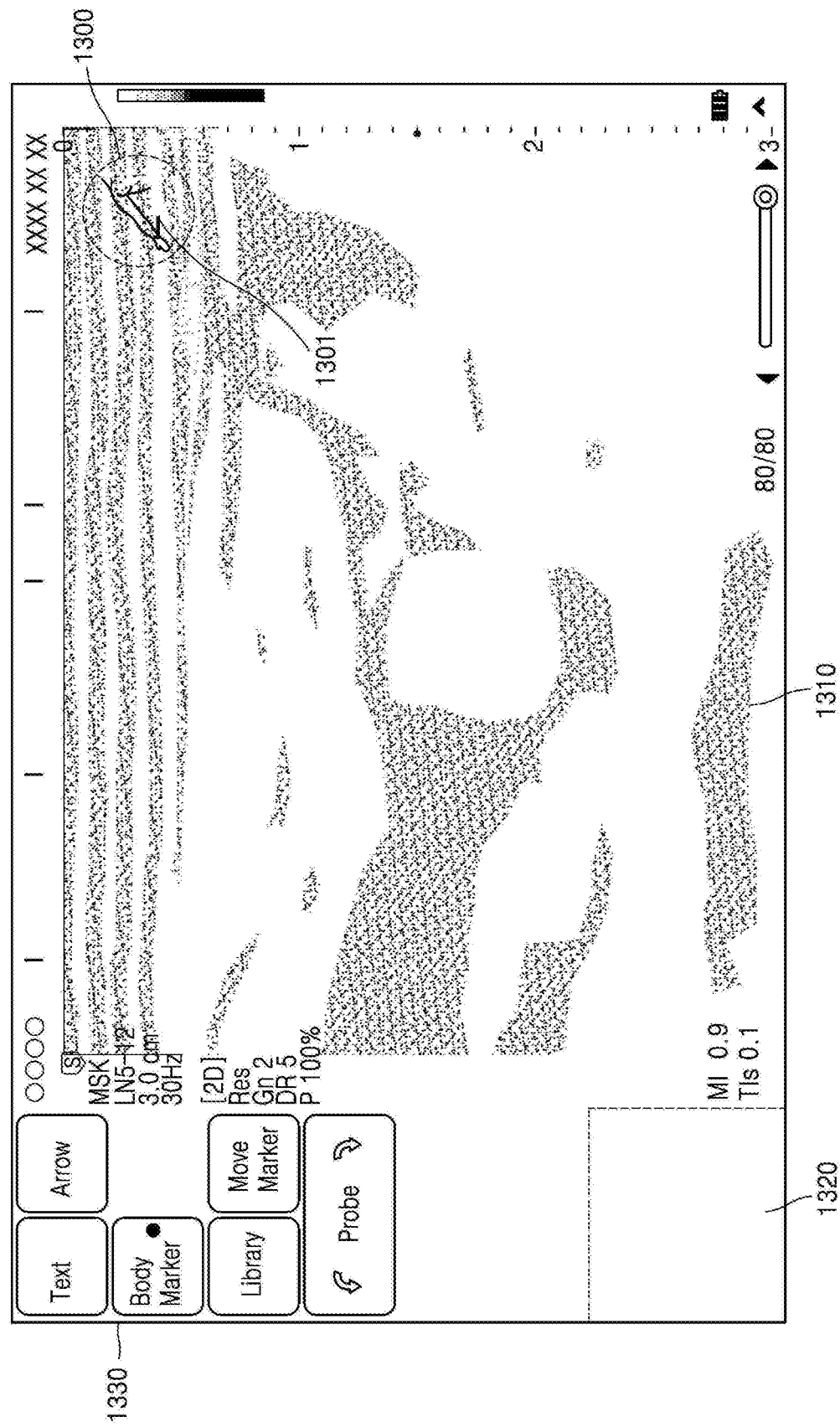

FIGS. 13A, 13B and 13C illustrate screens for providing a copy image related to generation of a body marker, performed by the ultrasound apparatus 100, according to an exemplary embodiment.

As illustrated in FIG. 13A, when a user selects a Body Marker button of a control panel that is displayed on a third area 1330, the ultrasound apparatus 100 may detect the user selection and may display a list of target figures indicating targets on a screen. For example, the list of target figures may include an arm figure, a leg figure, a womb figure, a heart figure, or the like.

When the user selects one target figure (e.g., the arm figure) from the list of target figures, the ultrasound apparatus 100 may display a body marker 1300 on an ultrasound image, wherein the body marker 1300 includes the selected target figure (i.e., the arm figure) and a probe FIG. 1301 indicating a probe position. In this case, the user may touch and simultaneously move the probe FIG. 1301 that indicates the probe position and that is included in the body marker 1300.

When the user touches the body marker 1300 by using a finger, the body marker 1300 and the probe FIG. 1301 indicating the probe position are obstructed by the finger. Thus, the ultrasound apparatus 100 may display a copy image having a predetermined size with respect to a user-touched portion on a second area 1320. The body marker 1300 that is displayed on the user-touched portion may be located at a center of the second area 1320. In particular, according to the present exemplary embodiment, the target figure that is included in the body marker 1300 may be located at the center of the second area 1320.

As illustrated in FIG. 13B, when the user touches and simultaneously moves the probe FIG. 1301 that indicates the probe position and that is included in the body marker 1300, in a lower left direction, the ultrasound apparatus 100 may change and display a position of the probe FIG. 1301, which indicates the probe position, in a copy image in real-time. According to the present exemplary embodiment, the target figure (e.g., the arm figure) may be constantly located at the center of the second area 1320, and only the position of the probe FIG. 1301 indicating the probe position may be changed as compared to FIG. 13A.

Thus, in the present exemplary embodiment, the user may recognize an exact position of the probe FIG. 1301, which is obstructed by a finger, in the first area 1310 by referring to the copy image displayed on the second area 1320.

As illustrated in FIG. 13C, when the user takes off the finger from the body marker 1300, the ultrasound apparatus 100 no longer displays the copy image of the body marker 1300, on the second area 1320.

In the present exemplary embodiment, the ultrasound apparatus 100 may allow the user to exactly recognize the probe FIG. 1301 by using the copy image, wherein the probe FIG. 1301 indicates the probe position and is obstructed by a touch instrument (e.g., a finger or an electronic pen), so that the ultrasound apparatus 100 may help the user to generate the body marker 1300 that exactly indicates a position of a target at which an ultrasound image is obtained.

Figure 14:
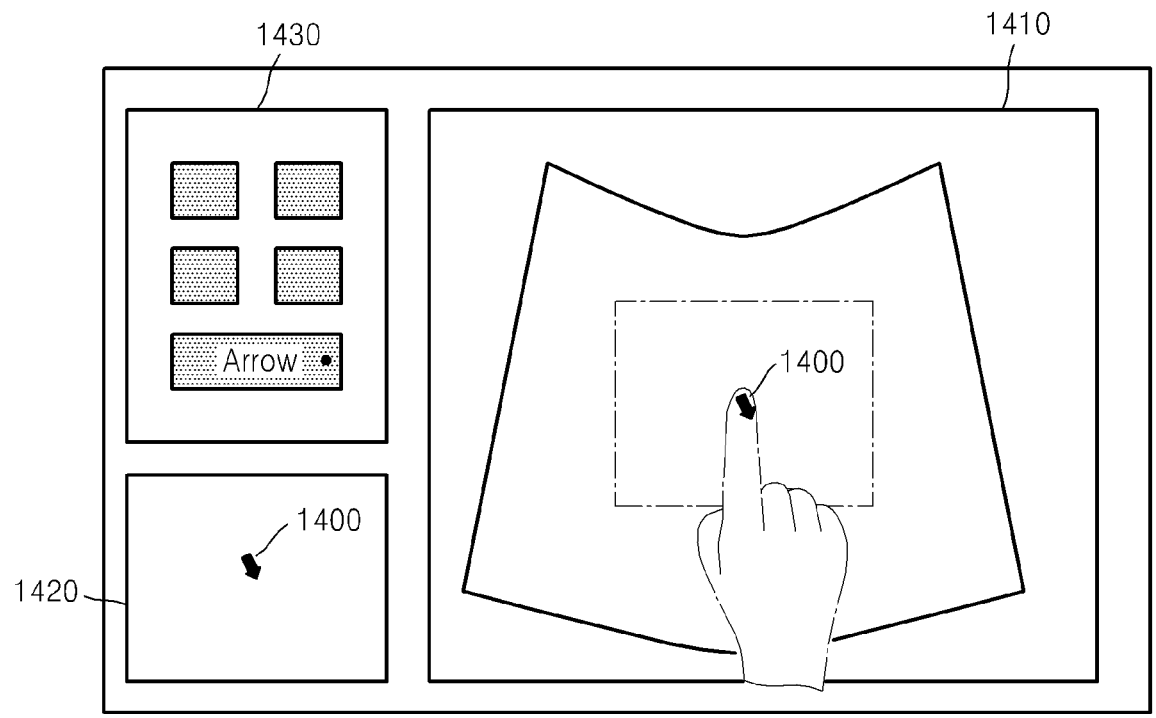
FIG. 14 illustrates a screen for providing a copy image related to an indication display, according to an exemplary embodiment.

FIG. 14 illustrates a screen for providing a copy image related to an indication display, performed by the ultrasound apparatus 100, according to an exemplary embodiment.

As illustrated in FIG. 14, when a user selects an Arrow button of a control panel that is displayed on a third area 1430, the ultrasound apparatus 100 may detect the user selection and may display an arrow 1400 on an ultrasound image. In this case, the user may touch and simultaneously move the arrow 1400 to a portion of an image (e.g., a possible tumor area, a finger of a fetus, or the like).

However, when the user touches the arrow 1400, the arrow 1400 and the ultrasound image around the arrow 1400 are obstructed by a finger. Thus, the ultrasound apparatus 100 may display a copy image having a predetermined size with respect to a user-touched portion, on a second area 1420. The arrow 1400 that is displayed on the user-touched portion may be located at a center of the second area 1420.

When the user touches and simultaneously drags the arrow 1400, a point at which a touch input is detected is continuously changed according to drag inputs, so that the ultrasound apparatus 100 may change a copy image in real-time with respect to the point at which the touch input is detected and may display the copy image on the second area 1420. The user may recognize an exact position of the arrow 1400, which is obstructed by a finger in the first area 1410, by referring to the copy image displayed on the second area 1420.

When the user moves the arrow 1400 to a user-desired position and then takes off the finger from the touch screen, the ultrasound apparatus 100 no longer displays the copy image on the second area 1420.

In an exemplary embodiment of FIG. 14, the arrow 1400 is described as an example of an indicator. However, in one or more exemplary embodiments, various types (e.g., a finger shape, a star shape, or the like) of the indicator may be used.

In the present exemplary embodiment, the ultrasound apparatus 100 may help the user to exactly recognize a position of the indicator, which is obstructed by a touch instrument (e.g., a finger or an electronic pen), by using the copy image.

Figure 15:
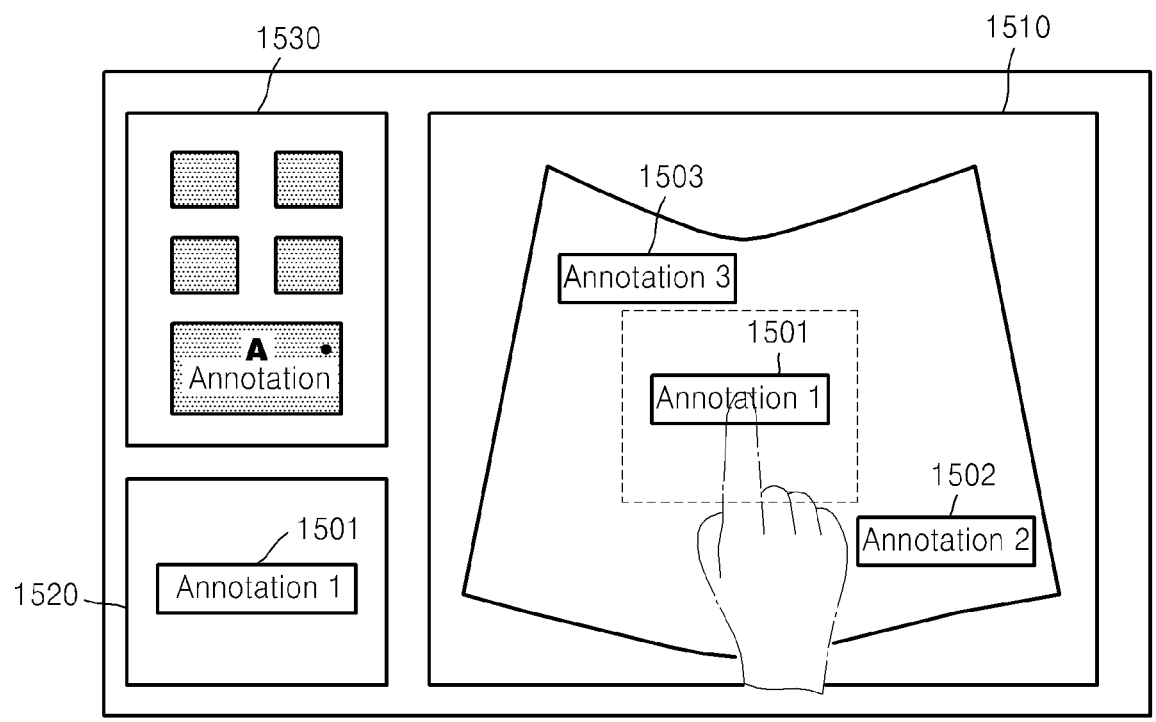
FIG. 15 illustrates a screen for providing a copy image and a plurality of activated objects related to annotation, according to an exemplary embodiment.

FIG. 15 illustrates a screen for providing a copy image and a plurality of activated objects related to an annotation, performed by the ultrasound apparatus 100, according to an exemplary embodiment.

As illustrated in FIG. 15, when a user selects an Annotation button of a control panel that is displayed on a third area 1530, the ultrasound apparatus 100 may detect the user selection and then may display a window for an input of a first annotation 1501 on an ultrasound image. In this case, the user may input the first annotation 1501, and may touch and simultaneously move the input first annotation 1501 to a target indication portion (e.g., a possible tumor area or the like).

However, when the user touches the first annotation 1501, the first annotation 1501 and an ultrasound image around the first annotation 1501 are obstructed by a finger. Thus, the ultrasound apparatus 100 may display a copy image having a predetermined size with respect to a user-touched portion, on a second area 1520. The first annotation 1501 that is displayed on the user-touched portion may be located at a center of the second area 1520.

When the user touches and simultaneously drags the first annotation 1501, a point at which a touch input is detected is continuously changed according to drag inputs, so that the ultrasound apparatus 100 may change a copy image in real-time with respect to the point at which the touch input is detected and may display the copy image on the second area 1520. The user may recognize an exact position of the first annotation 1501, which is obstructed by a finger in the first area 1510, by referring to the copy image displayed on the second area 1520.

When the user moves the first annotation 1501 to a user-desired position and then takes off the finger from the touch screen, the ultrasound apparatus 100 no longer displays the copy image on the second area 1520.

The ultrasound apparatus 100 may activate all of annotations 1501, 1502, and 1503 that are displayed on the screen. Thus, the user may freely change positions of the annotations 1502 and 1503 by touching and dragging the annotations 1502 and 1503.

In the present exemplary embodiment, the ultrasound apparatus 100 may help the user to exactly recognize the position of the annotation, which is obstructed by a touch instrument (e.g., a finger or an electronic pen), by using the copy image.

Figure 16:
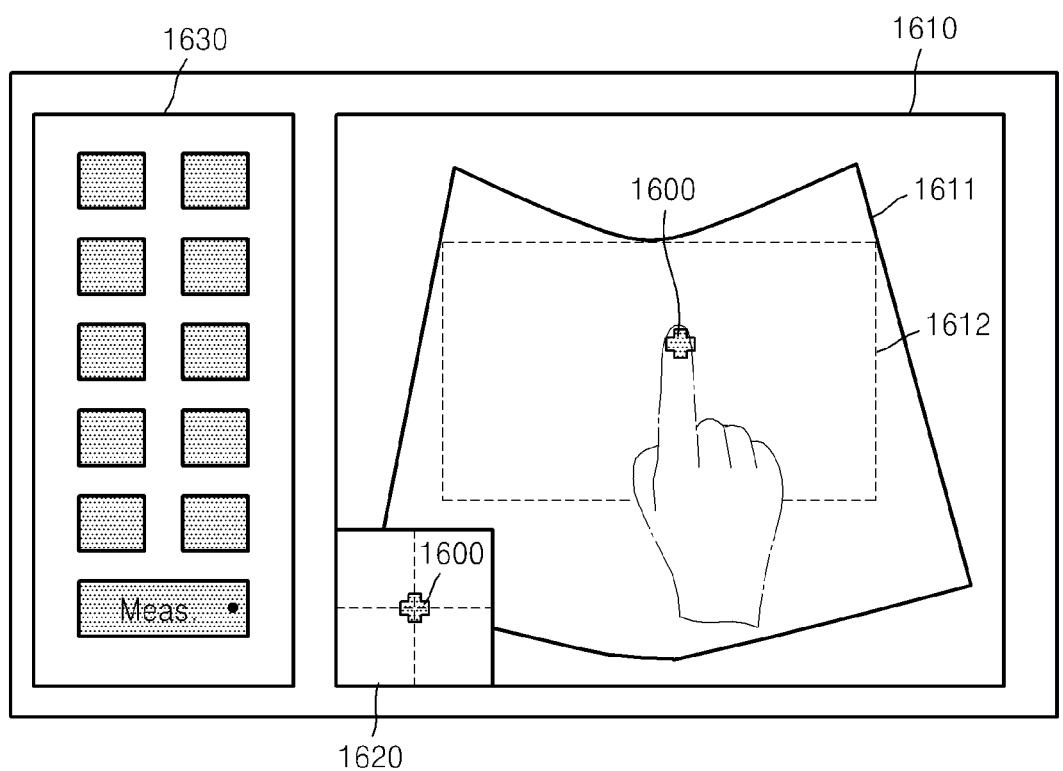
FIG. 16 illustrates a screen for displaying a copy image on a non-interest area of an ultrasound image, according to an exemplary embodiment.

FIG. 16 illustrates a screen for displaying a copy image on a non-interest area of an ultrasound image, performed by the ultrasound apparatus 100, according to an exemplary embodiment.

A second area 1620 on which the copy image is displayed may include a residual area of a first area 1610 on which an ultrasound image 1611 is displayed, wherein the residual area does not include an interest area 1612 of the first area 1610 which is selected by a user. The GUI is displayed on the third area 1630.

That is, the ultrasound apparatus 100 may display the copy image in the first area 1610 on which the ultrasound image 1611 is displayed, or may overlap the copy image with the first area 1610 and may display the copy image. For example, the ultrasound apparatus 100 may extract the non-interest area excluding the interest area 1612 of the ultrasound image 1611 that is displayed on a touch screen, and may display the copy image on the non-interest area.

The non-interest area may be the residual area excluding the interest area 1612 that is selected by the user. For example, in a mode for observing a fetus, the non-interest area may be a residual area excluding a predetermined area on which the fetus is displayed.

In the present exemplary embodiment, when the user takes off a touch instrument (e.g., a finger or an electronic pen) from the touch screen, the ultrasound apparatus 100 no longer displays the copy image that is displayed on the non-interest area.

Figure 17A:
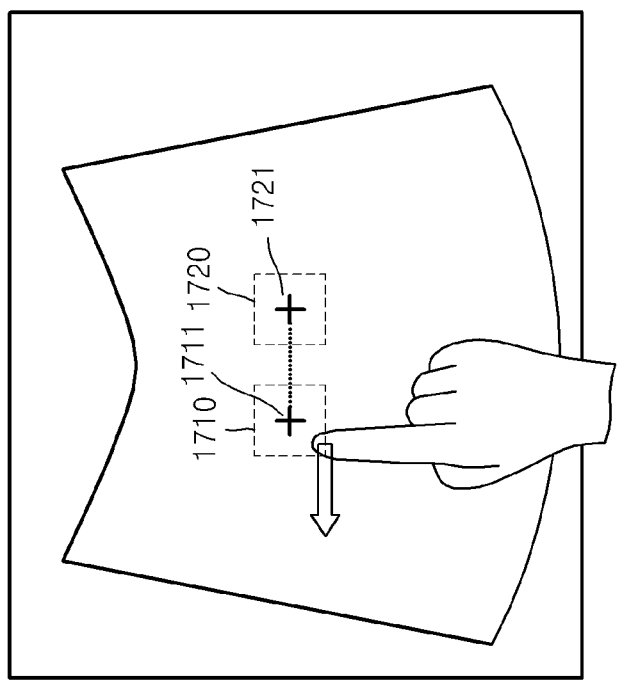
FIGS. 17A and 17B illustrate a touch recognition range with respect to an object, according to an exemplary embodiment.
Figure 17B:
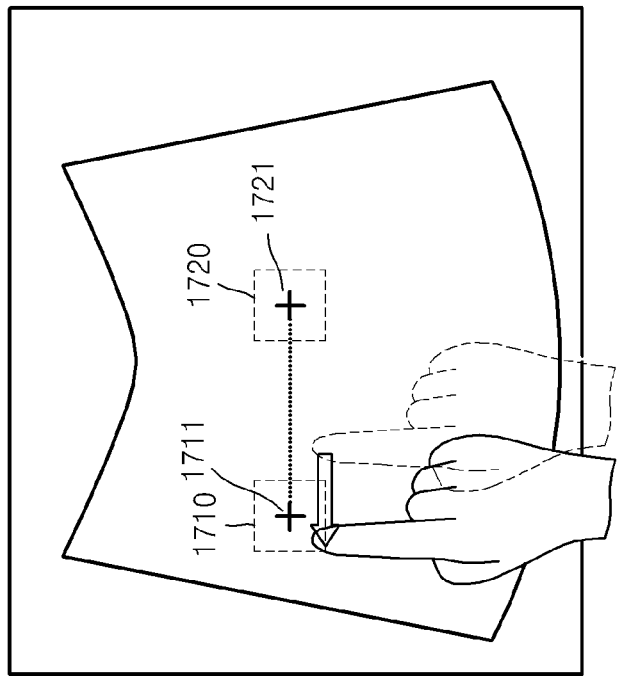

FIGS. 17A and 17B illustrate a touch recognition range with respect to an object, according to an exemplary embodiment.

As illustrated in FIG. 17A, a user may drag a first object 1711 away from a second object 1721 disposed in an area 1720 to increase a length of a measurement line. Although a user does not exactly touch a first object 1711, when the user touches a first area 1710 around the first object 1711, the ultrasound apparatus 100 may recognize that the first object 1711 is touched. That is, because the user might not exactly touch the object, or although the user exactly touches the object, an entire image of the object may be obstructed by a finger, or the like, the ultrasound apparatus 100 may expand the touch recognition range with respect to the object.

As illustrated in FIG. 17B, in a case where the user does not exactly touch the first object 1711 but touches and simultaneously drags the first area 1710 around the first object 1711 in a left direction, the ultrasound apparatus 100 may determine that the ultrasound apparatus 100 has received a touch and drag input with respect to the first object 1711, so that the ultrasound apparatus 100 may move the first object 1711 in the left direction and then may display the first object 1711.

FIGS. 18A, 18B, 19A and 19B illustrate cases in which touch recognition ranges of objects overlap with each other, according to an exemplary embodiment.

Figure 18B:
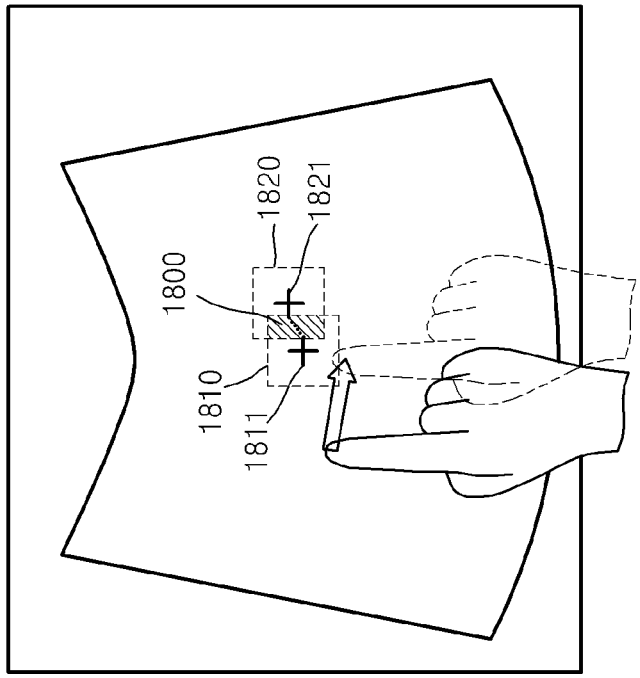
FIGS. 18A and 18B illustrate cases in which touch recognition ranges of objects overlap with each other, according to an exemplary embodiment.
Figure 18A:
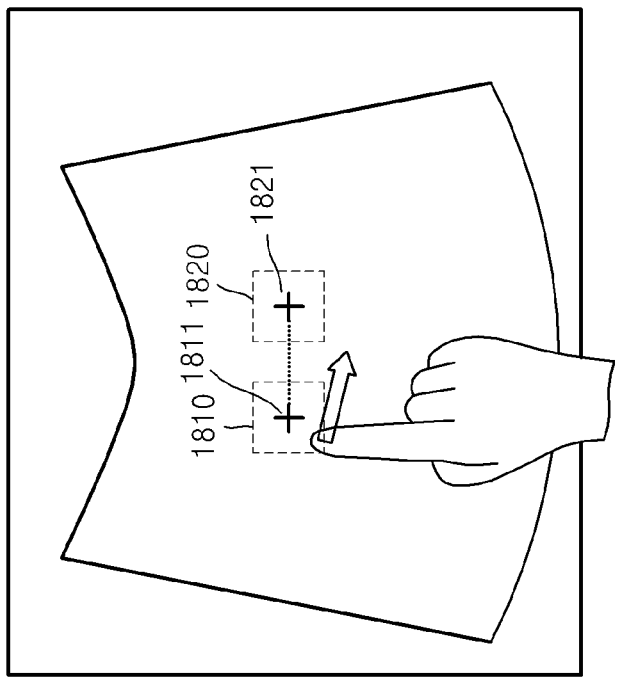

As illustrated in FIG. 18A, a user may drag a first object 1811 toward a second object 1821 to decrease a length of a measurement line. Here, when a distance between the first object 1811 and the second object 1821 is less than a predetermined distance, as illustrated in FIG. 18B, a touch recognition range 1810 of the first object 1811 and a touch recognition range 1820 of the second object 1821 may overlap with each other (area 1800).

As illustrated in FIG. 19A, when the user touches and drags an overlapped area 1900 in which a touch recognition range 1910 of the first object 1911 and a touch recognition range 1920 of the second object 1921 overlap with each other, the ultrasound apparatus 100 may move one of the first object 1911 and the second object 1921, based on priority order information.

For example, as illustrated in FIG. 19B, when a lastly-moved object has a priority, the ultrasound apparatus 100 may compare a movement time of the first object 1911 with a movement time of the second object 1921. When the movement time of the second object 1921 precedes the movement time of the first object 1911, the ultrasound apparatus 100 may move the first object 1911 according to a user's touch and drag input with respect to the overlapped area 1900.

Figure 20:
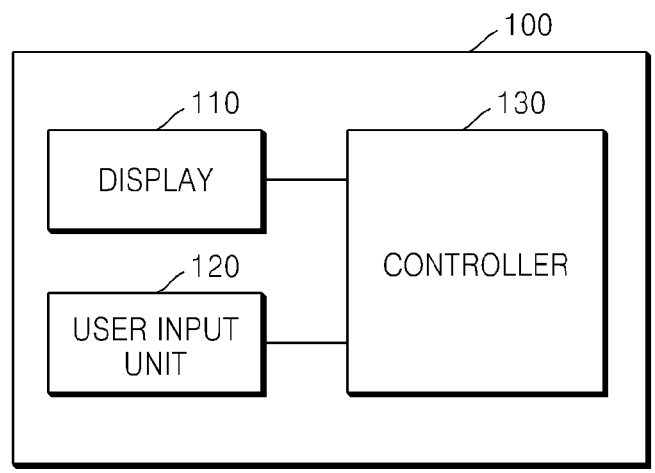
FIG. 20 is a block diagram illustrating a structure of the ultrasound apparatus, according to an exemplary embodiment.

FIG. 20 is a block diagram illustrating a structure of the ultrasound apparatus 100, according to an exemplary embodiment.

The ultrasound apparatus 100 may include the display 110, the user input unit 120, and a controller 130. However, not all shown elements are necessary elements. That is, the ultrasound apparatus 100 may be embodied with more or less elements than the shown elements.

Hereinafter, the aforementioned elements are described.

As described above, the display 110 and a touchpad may form a mutual layer structure and thus may be formed as a touch screen. That is, in the present exemplary embodiment, the display 110 may be used as both an output device and an input device.

The display 110 may display an ultrasound image on a first area of the touch screen. The display 110 may display a copy image on a second area that is different from the first area on which the ultrasound image is displayed. The display 110 may display the copy image on the second area so that an object that is displayed on the first area at a position at which a touch input is detected may be located at a center of the second area.

The display 110 may display a copy image of a partial image, which is changed according to drag inputs, on the second area of the touch screen. That is, according to the drag inputs by the user, the copy image that is displayed on the second area may be changed in real-time. The display 110 may move a predetermined object, which is dragged by the user, into the first area and then may display the predetermined object.

The display 110 may change a control panel for adjustment of parameter values related to the ultrasound image, according to a predetermined mode, and then may display the control panel on a third area of the touch screen.

Figure 22:
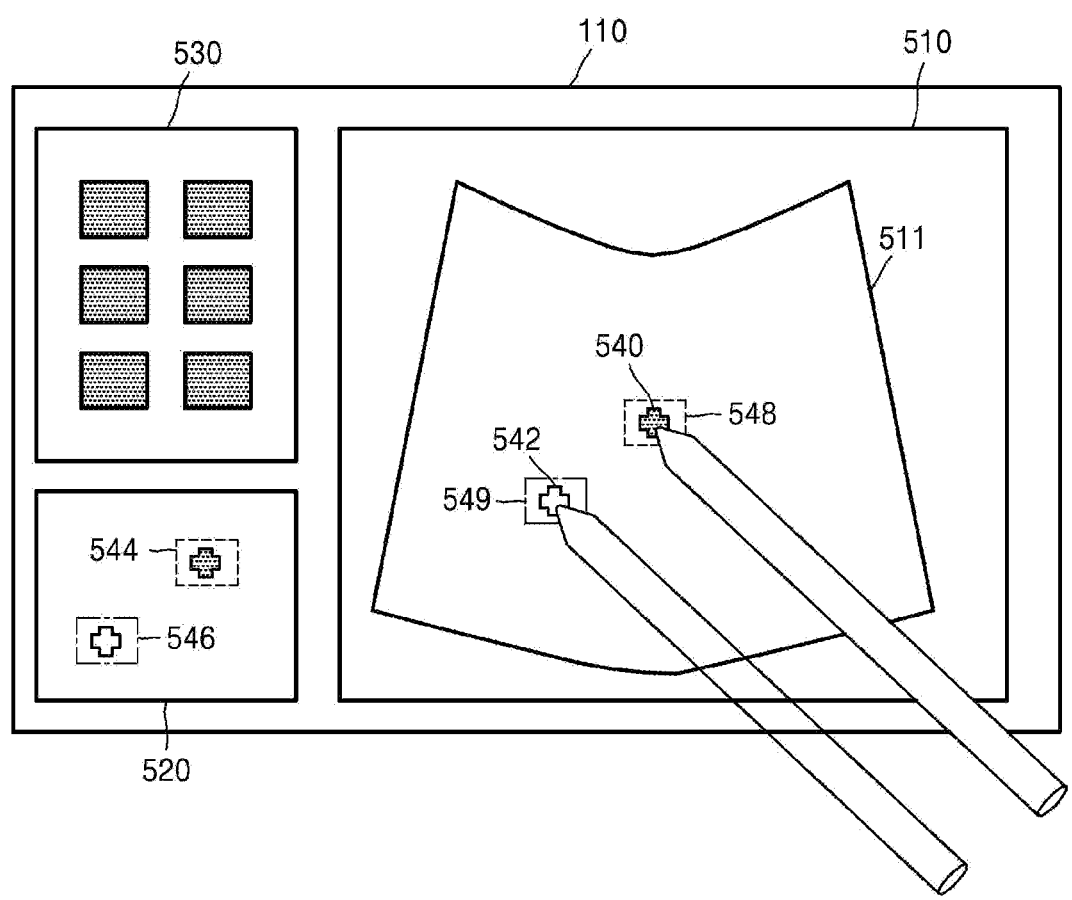
FIG. 22 illustrates a display of copy images, according to an exemplary embodiment.

The display 110 may display a plurality of copy images, as shown in FIG. 22. For example, when multiple touch inputs 540 and 542 are detected, the display 110 may display a plurality of copy images 544 and 546 about a plurality of partial images 548 and 549 on the second area 520, wherein the plurality of partial images correspond to at least two portions of the ultrasound image, respectively.

The display 110 may display a copy image on the second area, wherein the copy image is obtained by magnifying or reducing a partial image by a predetermined ratio.

The display 110 may display together a plurality of activated objects and the ultrasound image. The display 110 may display the activated objects to partially overlap with the ultrasound image, may display the activated objects on the ultrasound image, or may display the activated objects in an area of a screen which is different from another area of the screen on which the ultrasound image is displayed.

The display 110 may move at least one object from among the activated objects, according to a user's touch and drag input, and then may display the at least one object.

The display 110 may move and display a first object according to a touch and drag input with respect to the first area, and may move and display a second object according to a touch and drag input with respect to the second area. The first area may be an area in which the first object is recognized as being touched, and the second area may be an area in which the second object is recognized as being touched. That is, according to the present exemplary embodiment, the user may change a position of an object by touching an area around the object without exactly touching the object.

The display 110 may move and display each of the first and second objects according to multiple touch inputs.

The user input unit 120 is a means by which the user inputs data to control the ultrasound apparatus 100. For example, the user input unit 120 may be formed of, but is not limited to, a key pad, a dome switch, a touchpad (a touch capacitive type touchpad, a pressure resistive type touchpad, an infrared beam sensing type touchpad, a surface acoustic wave type touchpad, an integral strain gauge type touchpad, a Piezo effect type touchpad, or the like), a jog wheel, a jog switch, or the like. In particular, as described above, when a display panel and the touchpad form a layer structure, the structure may be a touch screen. In the present exemplary embodiment, the user input unit 120 may detect not only an actual touch but also may detect a proximate touch.

The user input unit 120 may detect a touch input (e.g., a touch and hold input, a tap input, a double-tap input, a flick input, a touch and drag input, or the like) with respect to an ultrasound image. The user input unit 120 may detect a drag input that starts at a position at which the touch input is first detected. The user input unit 120 may detect multiple touch inputs (e.g., a pinch input) with respect to at least two portions of the ultrasound image.

The user input unit 120 may receive a touch and drag input with respect to the first area within a predetermined radius from a point at which the first object from among the activated objects is displayed, and may receive a touch and drag input with respect to the second area within the predetermined radius from a point at which the second object from among the activated objects is displayed. A value of the predetermined radius may be set by the user or the ultrasound apparatus 100 and may be changed.

The user input unit 120 may receive a touch and drag input with respect to an area in which the first area and the second area overlap with each other.

The controller 130 controls operations of the ultrasound apparatus 100 and may include one or more processors. For example, the controller 130 may control the display 110 and the user input unit 120.

For example, the controller 130 may control the display 110 to extract a partial image of the ultrasound image that corresponds to the touch input, and then to display a copy image of the partial image on the second area that is different from the first area.

The controller 130 may obtain information about a position of the touch screen at which the touch input is detected, and may extract a partial image from the ultrasound image, wherein the partial image has a preset size with respect to the position at which the touch input is detected. The controller 130 may select the second area that is different from the first area on which the ultrasound image is displayed and that is different from the third area on which the control panel is displayed as a GUI.

When the controller 130 no longer detects a touch input, the controller 130 may remove the copy image from the second area. That is, when the user touches a specific portion of the ultrasound image and then takes off a finger from the ultrasound image, the copy image that is displayed on the second area may disappear.

The controller 130 may extract a plurality of objects that are movable during a predetermined mode, and may activate the objects so that each of the objects may be moved according to a user's touch input.

When the touch and drag input with respect to the area in which the first area and the second area overlap with each other is received, the controller 130 may control the display 110 to move and display one of the first and second objects based on the priority order information. For example, the controller 130 may compare movement time information of the first object with movement time information of the second object, and may control the display 110 to move and display one of the first and second objects, according to the comparison result.

Figure 21:
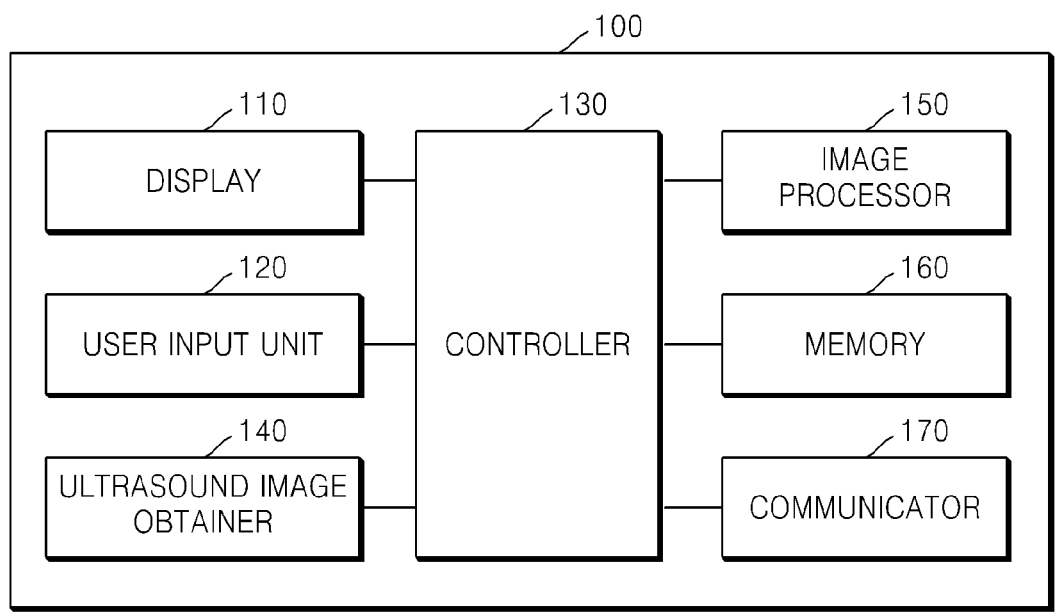
FIG. 21 is a diagram illustrating a structure of the ultrasound apparatus, according to an exemplary embodiment.

FIG. 21 is a diagram illustrating a structure of the ultrasound apparatus 100, according to an exemplary embodiment.

As illustrated in FIG. 21, the ultrasound apparatus 100 may include an ultrasound image obtainer 140, an image processor 150, a memory 160, and a communicator 170, in addition to the display 110, the user input unit 120, and the controller 130.

The ultrasound image obtainer 140 may include a probe (not shown) to transmit and receive an ultrasound signal, and a beamformer (not shown) to perform a transmit focusing operation and a receive focusing operation with respect to the ultrasound signal. In the present exemplary embodiment, the probe may include at least one of 1D (Dimension), 1.5D, 2D (matrix), and 3D probes.

The image processor 150 may capture a partial image corresponding to a touch input and then may generate a copy image of the partial image. When a touch input that is maintained over a predetermined time is detected, the image processor 150 may capture the partial image and then may generate the copy image. For example, when a touch input that is maintained over 2 seconds is detected, the image processor 150 may generate the copy image. The image processor 150 may capture the partial image at regular intervals or may capture the partial image when a position of the touch input is changed. A method of generating the copy image, performed by the image processor 150, is known to one of ordinary skill in the art related to the image processing technology; thus, detailed descriptions thereof are omitted.

The memory 160 may store a program for processing and controlling the controller 130, and/or pieces of data (e.g., a preset gain value, an ultrasound image, examinee information, probe information, a body marker, or the like) that are input/output.

The memory 160 may include a flash memory-type storage medium, a hard disk-type storage medium, a multimedia card micro-type storage medium, a card type memory (e.g., an SD card memory or an XD card memory), a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disc, and an optical disc. The ultrasound apparatus 100 may operate a web storage system that performs a storing function of the memory 160 over the Internet.

The communicator 170 may include one or more configuring elements that allow communication between the ultrasound apparatus 100 and an external device (not shown). For example, the communicator 170 may include a near field communication (NFC) module, a mobile communication module, a wireless internet module, a wired internet module, or the like.

The NFC module may include, but is not limited to, a wireless LAN (Wi-Fi), Bluetooth, BLE, Ultra Wideband (UWB), ZigBee, NFC, Wi-Fi Direct (WFD), and infrared Data Association (IrDA).

The mobile communication module exchanges a wireless signal with at least one of a base station, an external terminal, and a server via a mobile communication network. The wireless internet module is for accessing wireless Internet. The wireless internet module may be embedded in the ultrasound apparatus 100 or may be arranged outside the ultrasound apparatus 100. The wired internet module is for access to wired internet.

In the present exemplary embodiment, the communicator 170 may transmit the ultrasound image or the like to the external device. The external device may include, but is not limited to, a mobile phone, a smart phone, a laptop computer, a tablet PC, an electronic book terminal, a terminal for digital broadcasting, a personal digital assistant (PDA), a portable multimedia player (PMP), a digital camera, or the like.

An exemplary embodiment may also be embodied as programmed commands to be executed by various computer means, and may then be recorded in a computer-readable recording medium. The computer-readable recording medium may include one or more of the programmed commands, data files, data structures, or the like. The programmed commands recorded to the computer-readable recording medium may be particularly designed or configured for exemplary embodiments or may be of those well known to one of ordinary skill in the art. Examples of the computer-readable recording medium include magnetic media including hard disks, magnetic tapes, and floppy disks, optical media including CD-ROMs, and DVDs, magneto-optical media including optical disks, and a hardware apparatus designed to store and execute the programmed commands in read-only memory (ROM), random-access memory (RAM), flash memories, and the like. Examples of the programmed commands include not only machine codes generated by a compiler but also include codes to be executed in a computer by using an interpreter.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ultrasound measurement method comprising:
   providing, on an ultrasound image, a first measurement mark and a second measurement mark, and visual indicators which define a first expanded touch recognition range and a second expanded touch recognition range for the first measurement mark and the second measurement mark, respectively;
   receiving a first touch and drag input on at least a portion of at least one from among the first expanded touch recognition range and the second expanded touch recognition range;
   moving at least one from among the first measurement mark and the second measurement mark, based on the first touch and drag input, to change a distance between the first measurement mark and the second measurement mark;
   displaying the at least one from among the first measurement mark and the second measurement mark that have been moved, at a new position; and
   providing a measurement result of a distance between the first measurement mark and the second measurement mark,
   wherein the providing the first measurement mark and the second measurement mark comprises providing each of the first measurement mark and the second measurement mark in a center point within each of the visual indicators, respectively,
   wherein the displaying the at least one from among the first measurement mark and the second measurement mark comprises, when the distance between the first measurement mark and the second measurement mark is changed, displaying the first measurement mark and the second measurement mark at the center point of each of the visual indicators, respectively, and
   wherein each of the first measurement mark and the second measurement mark remains centered within each of the visual indicators, respectively, when the distance between the first measurement mark and the second measurement mark becomes smaller such that the first expanded touch recognition range overlaps the second expanded touch recognition range based on the moving the at least one from among the first measurement mark and the second measurement mark, and when the distance between the first measurement mark and the second measurement mark becomes greater based on the moving the at least one from among the first measurement mark and the second measurement mark.

2. The ultrasound measurement method according to claim 1, further comprising:
   displaying a graphical line connecting the first measurement mark and the second measurement mark.

3. The ultrasound measurement method according to claim 2, further comprising:
   continuing to display the graphical line connecting the first measurement mark and the second measurement mark before, during and after the moving the at least one from among the first measurement mark and the second measurement mark.

4. The ultrasound measurement method according to claim 1, further comprising:
   based on a user input, providing four measurement marks comprising a third measurement mark, a fourth measurement mark, a fifth measurement mark, and a sixth measurement mark within the displayed ultrasound image;
   activating the four measurement marks together, to be movable on the ultrasound image; and
   defining a shape of a measurement area by displacing at least one from among the third measurement mark, the fourth measurement mark, the fifth measurement mark, and the sixth measurement mark based on a second touch and drag input,
   wherein the user input is a different input from the first touch and drag input.

5. The ultrasound measurement method according to claim 4, wherein the third measurement mark and the fourth measurement mark are disposed on a boundary of the measurement area opposite one another in a first direction;
   the fifth measurement mark and the sixth measurement mark are disposed on the boundary of the measurement area opposite one another in a second direction different from the first direction;
   the defining comprises defining the shape of the measurement area as an ellipse by displacing at least one from among the third measurement mark and the fourth measurement mark or at least one from among the fifth measurement mark and the sixth measurement mark; and
   the four measurement marks remain activated during the defining of the ellipse.

6. The ultrasound measurement method according to claim 1, further comprising:
   activating the first measurement mark and the second measurement mark to be movable to perform a measurement on the ultrasound image.

7. The ultrasound measurement method according to claim 1, further comprising:
   receiving a second touch and drag input on a portion of a touch screen where the first expanded touch recognition range overlaps the second expanded touch recognition range, the second touch and drag input corresponding to the first expanded touch recognition range or the second expanded touch recognition range, and
   moving one from among the first measurement mark and the second measurement mark, based on priority order information.

8. The ultrasound measurement method according to claim 7, wherein the moving the one from among the first measurement mark and the second measurement mark comprises:

comparing movement time information of the first measurement mark with movement time information of the second measurement mark; and moving the one from among the first, measurement mark and the second measurement mark according to a result of the comparing.

9. The ultrasound measurement method according to claim 8, wherein the moving the one from among, the first measurement mark and the second measurement mark further comprises:

moving a most recently moved measurement mark among the first measurement mark and the second measurement mark.

10. The ultrasound measurement method according to claim 1, further comprising:

receiving an input of a measurement instruction, from a user; and receiving an input of a selection of a measurement shape, from the user.

11. The ultrasound measurement method according to claim 1, wherein the providing the first measurement mark and the second measurement mark further comprises providing, within the ultrasound image, a plurality of measurement marks which include the first measurement mark and the second measurement mark, and the ultrasound measurement method further comprises:
providing, on a touch screen, a shape outline on which the plurality of measurement marks are displayed, the shape outline being a graphical line;
activating the plurality of measurement marks together, to be movable on the ultrasound image; and
deforming the shape outline to define a measurement area by displacing at least one of the plurality of measurement marks based on a second touch and drag input.

12. The ultrasound measurement method according to claim 1, further comprising:

receiving multiple touch and drag inputs on the first measurement mark and the second measurement mark; and moving each of the first measurement mark and the second measurement mark according to the multiple touch and drag inputs.

13. The ultrasound measurement method according to claim 1, wherein the first measurement mark and the second measurement mark are movable during at least one from among a measurement mode, an annotation input mode, a Doppler mode, and an M mode.

14. The ultrasound measurement method according to claim 1, further comprising:

activating the first measurement mark and the second measurement mark to be movable to perform a measurement on the ultrasound image.

15. A non-transitory computer-readable medium having recorded thereon program instructions which, when executed by a computer, cause the computer to execute the ultrasound measurement method of claim 1.

16. An ultrasound apparatus comprising:

a touch screen configured to display an ultrasound image and receive a touch input on the ultrasound image; and a controller configured to:
provide, on the ultrasound image, a first measurement mark and a second measurement mark, and visual indicators which define a first expanded touch recognition range and a second expanded touch recognition range for the first measurement mark and the second measurement mark, respectively,
receive a first touch and drag input on at least a portion of at least one from among the first expanded touch recognition range and the second expanded touch recognition range,
move at least one from among the first measurement mark and the second measurement mark, based on the first touch and drag input, to change a distance between the first measurement mark and the second measurement mark,
display the at least one from among the first measurement mark and the second measurement mark that have been moved, at a new position, and
provide a measurement result of a distance between the first measurement mark and the second measurement mark, wherein the controller is further configured to:
provide each of the first measurement mark and the second measurement mark in a center point within each of the visual indicators, respectively, and
when the distance between the first measurement mark and the second measurement mark is changed, display the first measurement mark and the second measurement mark at the center point of each of the visual indicators, respectively, wherein each of the first measurement mark and the second measurement mark remains centered within each of the visual indicators, respectively, when the distance between the first measurement mark and the second measurement mark becomes smaller such that the first expanded touch recognition range overlaps the second expanded touch recognition range based on the moving the at least one from among the first measurement mark and the second measurement mark, and when the distance between the first measurement mark and the second measurement mark becomes greater based on the moving the at least one from among the first measurement mark and the second measurement mark.

* * * * *